(12) United States Patent
Imagawa et al.

(10) Patent No.: US 11,191,504 B2
(45) Date of Patent: Dec. 7, 2021

(54) X-RAY DIAGNOSIS APPARATUS COMPRISING A BLOOD VESSEL RUNNING INFORMATION ACQUIRING FUNCTION, A POSITION SPECIFICATION FUNCTION, AND A DIAPHRAGM CONTROL FUNCTION

(71) Applicant: Canon Medical Systems Corporation, Otawara (JP)

(72) Inventors: Kazuo Imagawa, Nasushiobara (JP); Shingo Abe, Nasushiobara (JP); Akihito Takahashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 16/525,762

(22) Filed: Jul. 30, 2019

(65) Prior Publication Data

US 2020/0037972 A1     Feb. 6, 2020

(30) Foreign Application Priority Data

Jul. 31, 2018   (JP) .............................. JP2018-143752
Jul. 23, 2019   (JP) .............................. JP2019-135059

(51) Int. Cl.
    *A61B 6/00*        (2006.01)
    *A61B 6/06*        (2006.01)
    *A61B 6/03*        (2006.01)

(52) U.S. Cl.
CPC .............. *A61B 6/504* (2013.01); *A61B 6/035* (2013.01); *A61B 6/06* (2013.01); *A61B 6/40* (2013.01);

(Continued)

(58) Field of Classification Search
CPC ........... A61B 6/032; A61B 6/035; A61B 6/06; A61B 6/12; A61B 6/40; A61B 6/4035;

(Continued)

(56) References Cited

U.S. PATENT DOCUMENTS 5,278,887 A * 1/1994 Chiu ........................ G21K 1/10
                                                                378/156
5,282,254 A * 1/1994 Chiu ........................ A61B 6/06
                                                                 378/159

(Continued)

FOREIGN PATENT DOCUMENTS

JP    2000-342565 A    12/2000
JP    2009-106547 A    5/2009
JP    2014-144053 A    8/2014

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray diagnosis apparatus includes an X-ray generator, an X-ray diaphragm, an X-ray detector, an image capturing unit, a blood vessel running information acquiring unit, a device position specifying unit, and a diaphragm controller. The X-ray generator emits X-rays. The X-ray diaphragm restricts a region to be irradiated with X-rays emitted from the X-ray generator. The X-ray detector detects X-rays emitted from the X-ray generator. The image capturing unit acquires an X-ray image based on a detection result obtained by the X-ray detector. The blood vessel running information acquiring unit acquires blood vessel running information. The device position specifying unit specifies the position of a device in the X-ray image. The diaphragm controller controls the X-ray diaphragm based on the blood vessel running information and the position of the device.

17 Claims, 15 Drawing Sheets

(52) U.S. Cl.
CPC .......... *A61B 6/4035* (2013.01); *A61B 6/4042* (2013.01); *A61B 6/42* (2013.01); *A61B 6/4208* (2013.01); *A61B 6/4233* (2013.01); *A61B 6/44* (2013.01); *A61B 6/4429* (2013.01); *A61B 6/4435* (2013.01); *A61B 6/4441* (2013.01); *A61B 6/4447* (2013.01); *A61B 6/46* (2013.01); *A61B 6/461* (2013.01); *A61B 6/465* (2013.01); *A61B 6/467* (2013.01); *A61B 6/486* (2013.01); *A61B 6/487* (2013.01); *A61B 6/488* (2013.01); *A61B 6/5205* (2013.01); *A61B 6/5211* (2013.01); *A61B 6/54* (2013.01); *A61B 6/542* (2013.01); *A61B 6/545* (2013.01); *A61B 6/032* (2013.01); *A61B 6/463* (2013.01); *A61B 6/469* (2013.01); *A61B 6/481* (2013.01); *G06T 2207/10116* (2013.01)

(58) Field of Classification Search
CPC ....... A61B 6/4042; A61B 6/42; A61B 6/4208; A61B 6/4233; A61B 6/44; A61B 6/4429; A61B 6/4435; A61B 6/4441; A61B 6/4447; A61B 6/46; A61B 6/461; A61B 6/467; A61B 6/469; A61B 6/481; A61B 6/486; A61B 6/487; A61B 6/488; A61B 6/52; A61B 6/5205; A61B 6/5211; A61B 6/542; A61B 6/504; A61B 6/54; A61B 6/544; A61B 6/545
USPC .............. 378/15, 42, 62, 98, 147, 150, 151, 378/156–159
See application file for complete search history.

(56) References Cited

U.S. PATENT DOCUMENTS

| | | | | |
|---|---|---|---|---|
| 5,293,574 A * | 3/1994 | Roehm | | A61B 6/504 |
| | | | | 348/E5.046 |
| 5,369,678 A * | 11/1994 | Chiu | | A61B 6/06 |
| | | | | 378/152 |
| 6,463,121 B1 * | 10/2002 | Milnes | | A61B 6/469 |
| | | | | 378/62 |
| 6,619,839 B2 * | 9/2003 | Yoshimura | | A61B 6/0478 |
| | | | | 378/195 |
| 7,133,492 B2 * | 11/2006 | Kramp | | A61B 6/04 |
| | | | | 378/62 |
| 7,283,614 B2 * | 10/2007 | Nakano | | A61B 6/4441 |
| | | | | 378/62 |
| 7,406,148 B2 * | 7/2008 | Russinger | | A61B 6/504 |
| | | | | 378/15 |
| 7,522,701 B2 * | 4/2009 | Jensen | | A61B 6/481 |
| | | | | 378/162 |
| 7,580,502 B2 * | 8/2009 | Dalpiaz | | A61B 6/14 |
| | | | | 378/38 |
| 8,351,574 B2 * | 1/2013 | Takemoto | | A61B 6/501 |
| | | | | 378/98 |
| 9,125,572 B2 * | 9/2015 | Noo | | A61B 6/027 |
| 9,198,626 B2 * | 12/2015 | Heuscher | | A61B 6/482 |
| 9,259,191 B2 * | 2/2016 | Noo | | G21K 1/02 |
| 9,332,946 B2 * | 5/2016 | Heuscher | | A61B 6/405 |
| 9,888,899 B2 * | 2/2018 | Shimizu | | A61B 6/06 |
| 9,936,933 B2 * | 4/2018 | Lim | | A61B 6/469 |
| 10,010,373 B2 * | 7/2018 | Canfield | | A61B 18/1492 |
| 10,039,518 B2 * | 8/2018 | Kieft | | A61B 6/12 |
| 10,085,706 B2 * | 10/2018 | Kang | | A61B 6/542 |
| 10,441,239 B2 * | 10/2019 | Abe | | A61B 6/542 |
| 10,568,587 B2 * | 2/2020 | Ohishi | | G06T 7/0012 |
| 10,575,809 B2 * | 3/2020 | Akiyama | | A61B 6/4441 |
| 10,610,180 B2 * | 4/2020 | Ashida | | A61B 6/5217 |
| 10,631,797 B2 * | 4/2020 | Abe | | A61B 6/5217 |
| 10,674,982 B2 * | 6/2020 | Barak | | A61B 6/025 |
| 10,702,226 B2 * | 7/2020 | Barak | | A61B 6/12 |
| 10,733,753 B2 * | 8/2020 | Furuichi | | A61B 6/032 |
| 10,736,588 B2 * | 8/2020 | Van Dijk | | A61B 6/54 |
| 10,743,832 B2 * | 8/2020 | Schouten | | A61B 6/467 |
| 10,779,775 B2 * | 9/2020 | Bergman | | A61B 6/487 |
| 2015/0139394 A1 | 5/2015 | Kang et al. | | |

* cited by examiner

FIG. 6

| SHAPE OF BLOOD VESSEL | | | MOVEMENT AMOUNT OF ROI | SIZE OF ROI | SHAPE OF ROI |
|---|---|---|---|---|---|
| DIAMETER | | A1 | X11 | Y11 | Z11 |
| | | A2 | X12 | Y12 | Z12 |
| | | A3 | X13 | Y13 | Z13 |
| | BRANCH | B1 | X14 | Y14 | Z14 |
| | | B2 | X15 | Y15 | Z15 |
| | | B3 | X16 | Y16 | Z16 |

US 11,191,504 B2

X-RAY DIAGNOSIS APPARATUS COMPRISING A BLOOD VESSEL RUNNING INFORMATION ACQUIRING FUNCTION, A POSITION SPECIFICATION FUNCTION, AND A DIAPHRAGM CONTROL FUNCTION

CROSS-REFERENCE TO RELATED APPLICATION

This application is based upon and claims the benefit of priority from Japanese Patent Applications No. 2018-143752, filed Jul. 31, 2018 and No. 2019-135059, filed on Jul. 23, 2019; the entire contents of which are incorporated herein by reference.

FIELD

Embodiments described herein relate generally to an X-ray diagnosis apparatus.

BACKGROUND

The X-ray diagnosis apparatus is used for, for example, examinations and treatments of cardiovascular diseases. In many cases, a device is used in such examinations and treatments using the X-ray diagnosis apparatus. Examples of the device include a catheter for injecting a contrast agent, a thrombolytic agent, or the like, a balloon catheter for radially expanding a stenosis site, a stent for keeping the diameter of a blood vessel expanded by the balloon catheter, a catheter having at its tip a micro-cutter that is moved or rotated within a blood vessel to remove deposits (plaques) from a stenosis site in directional coronary atherectomy (DCA), a rotablator, and the like.

In X-ray images captured by the X-ray diagnosis apparatus, a region of interest may sometimes be set to indicate a region that a doctor or the like focuses on.

BRIEF DESCRIPTION OF THE DRAWINGS

FIG. 6 is an example of a table in which blood vessel running information is associated with information on the region of interest;

DETAILED DESCRIPTION

In general, according to one embodiment, an X-ray diagnosis apparatus includes an X-ray generator, an X-ray diaphragm, an X-ray detector, an image capturing unit, a blood vessel running information acquiring unit, a device position specifying unit, and a diaphragm controller. The X-ray generator emits X-rays. The X-ray diaphragm restricts a region to be irradiated with X-rays emitted from the X-ray generator. The X-ray detector detects X-rays emitted from the X-ray generator. The image capturing unit acquire an X-ray image based on a detection result obtained by the X-ray detector. The blood vessel running information acquiring unit acquires blood vessel running information. The device position specifying unit specifies the position of a device in the X-ray image. The diaphragm controller controls the X-ray diaphragm based on the blood vessel running information and the position of the device.

First Embodiment

In the following, a first embodiment is described with reference to the drawings.

Figure 1:
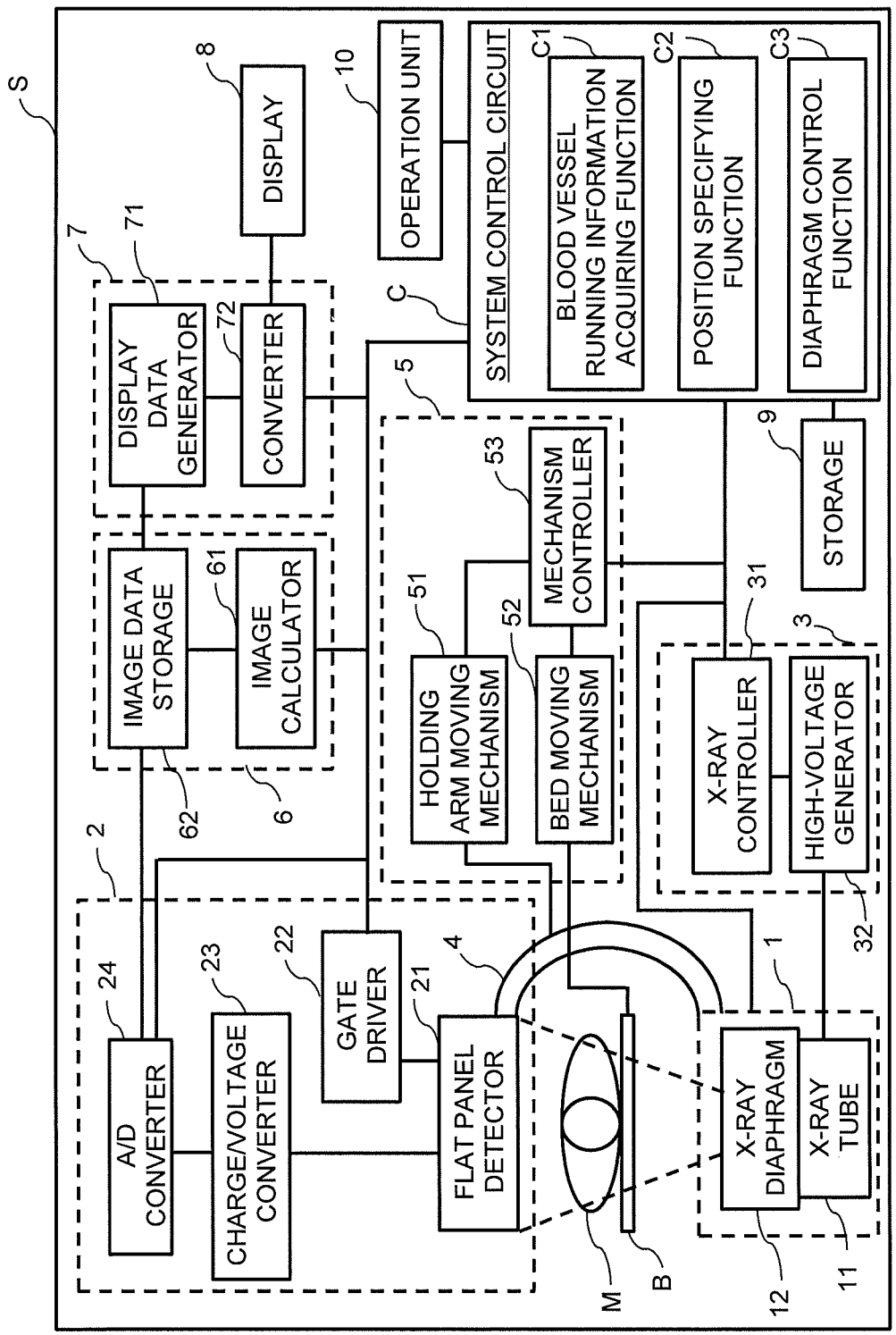
FIG. 1 is a block diagram illustrating the configuration of an X-ray diagnosis apparatus according to a first embodiment.

FIG. 1 is a block diagram illustrating the configuration of an X-ray diagnosis apparatus S of the first embodiment. The X-ray diagnosis apparatus S of the first embodiment includes an X-ray generator 1, an X-ray detector 2, and a high-voltage generating unit 3. The high-voltage generating unit 3 generates a high voltage necessary for X-ray irradiation by the X-ray generator 1. The X-ray generator 1 and the X-ray detector 2 are respectively arranged at both ends of a holding arm 4. The holding arm 4 has, for example, a C-shaped body (C arm).

The X-ray diagnosis apparatus S further includes a mechanism unit 5, an image capturing unit 6, a display controller 7, and a display 8. The mechanism unit 5 is configured to move the holding arm 4 and a bed B. The image capturing unit 6 is configured to acquire and store X-ray transmission information detected by the X-ray detector 2 as an image. The display controller 7 is configured to control the display of X-ray image data acquired by the image capturing unit 6 on the display. The display 8 displays, for example, images and imaging conditions generated by the display controller 7.

The X-ray diagnosis apparatus S further includes a storage 9, an operation unit 10, and a system control circuit C. The storage 9 stores, for example, blood vessel running information acquired by the own apparatus or acquired from another apparatus. The operation unit 10 is used by a medical worker to provide various instructions to the X-ray diagnosis apparatus S. The system control circuit C controls each unit of the X-ray diagnosis apparatus S.

The X-ray generator 1 includes an X-ray tube 11 configured to irradiate a subject M with X-rays, and an X-ray diaphragm 12 configured to adjust the irradiation range of X-rays emitted from the X-ray tube 11 to the subject M. The X-ray tube 11 is a vacuum tube that generates X-rays. The X-ray tube 11 accelerates electrons emitted from a cathode (filament) with a high voltage such that the accelerated electrons collide with a tungsten anode, thereby generating X-rays. The X-ray diaphragm 12 is located between the X-ray tube 11 and the subject M. The X-ray diaphragm 12 is an example of the X-ray diaphragm mechanism having a function to adjust X-ray beams emitted from the X-ray tube 11 to a position and a size according to the imaging region or the movement of a device.

In response to X-ray irradiation, the X-ray detector 2 detects X-rays. The X-ray detector 2 includes a flat panel detector 21, a gate driver 22, a charge/voltage converter 23, and an A/D converter 24.

The flat panel detector 21 converts X-rays that have transmitted through the subject M into a charge and stores the charge. The flat panel detector 21 is formed of, for example, minute detection elements arranged two-dimensionally in the column direction and the line direction. With this, each of the detection elements senses X-rays and generates a charge according to the amount of the incident X-rays. The flat panel detector 21 sends the charge to the charge/voltage converter 23.

The gate driver 22 supplies a drive voltage to the gate terminal of a thin film transistor (TFT) to retrieve the charge stored in the flat panel detector 21 as an X-ray image signal. The charge/voltage converter 23 converts the charge retrieved from the flat panel detector 21 into a voltage. The A/D converter 24 converts the output of the charge/voltage converter 23 into a digital signal.

The high-voltage generating unit 3 generates a high voltage for the X-ray generator 1 to emit X-rays. The high-voltage generating unit 3 includes an X-ray controller 31 and a high-voltage generator 32. The X-ray controller 31 outputs, to the high-voltage generator 32, a control signal related to X-ray irradiation conditions such as tube current, tube voltage, and irradiation time in the X-ray tube 11 based on the input from the system control circuit C. The X-ray controller 31 is an example of the X-ray control function. The high-voltage generator 32 applies a high voltage between the anode and the cathode of the X-ray tube 11 based on the input from the X-ray controller 31.

The holding arm 4 connects and holds the X-ray generator 1 and the X-ray detector 2. The X-ray generator 1 and the X-ray detector 2 are arranged at both ends of the holding arm 4, which is a C-arm, at positions facing each other with the bed B between them. In this manner, the holding arm 4 is provided with these devices at both the ends, and is movable according to imaging conditions. Since the X-ray detector 2 detects X-rays that have been irradiated and transmitted through the subject M, the X-ray generator 1 and the X-ray detector 2 arranged at both ends of the C arm are located at opposite positions across the subject M (the bed B).

In the X-ray diagnosis apparatus S illustrated in FIG. 1, the X-ray generator 1 is located below the bed B, i.e., at a position close to the surface where the X-ray diagnosis apparatus S is installed. On the other hand, the X-ray detector 2 is located above the bed B.

The mechanism unit 5 drives the mechanism of each part of the X-ray diagnosis apparatus S. The mechanism unit 5 includes, for example, a holding arm moving mechanism 51, a bed moving mechanism 52, and a mechanism controller 53 that controls each of the mechanisms.

The holding arm moving mechanism 51 moves the holding arm 4. For example, the holding arm moving mechanism 51 moves the X-ray generator 1 and the X-ray detector 2 relative to the body axis direction of the subject M. The bed moving mechanism 52 moves the bed B horizontally or vertically.

The mechanism controller 53 controls the drive of the mechanism unit 5 that includes the holding arm moving mechanism 51 and the bed moving mechanism 52 according to a control signal from a system control circuit C (described later).

While the mechanism unit 5 has been described as having the holding arm moving mechanism 51, the bed moving mechanism 52, and the mechanism controller 53, it is only an example. The mechanism unit 5 may include other mechanisms.

The image capturing unit 6 acquires an X-ray image based on detection results obtained by the X-ray detector 2. The image capturing unit 6 is an example of the image capturing function/mechanism. The image capturing unit 6 includes an image calculator 61 and an image data storage 62. The image calculator 61 receives X-ray transmission information acquired by the X-ray detector 2, and performs image processing operation for enhancing the contour and improving the S/N ratio based on the X-ray transmission information. The image calculator 61 is an example of the image processing function. The image data storage 62 temporarily stores X-ray image data obtained by the image processing operation of the image calculator 61.

The display controller 7 converts the X-ray image data acquired by the image capturing unit 6 to generate X-ray image data to be displayed on the display 8 as display data. The display controller 7 includes a display data generator 71 and a converter 72. The display data generator 71 acquires X-ray image data from the image capturing unit 6 and generates X-ray image data as display data. The converter 72 converts the generated X-ray image data into an X-ray image to be displayed.

The display 8 is, for example, a liquid crystal display. The display 8 receives an output signal from the system control circuit C, and displays, for example, an X-ray image that contains a device necessary for a procedure by a doctor, or an image and the like necessary for setting conditions to request the X-ray diagnosis apparatus S to process a particular image.

The storage 9 is formed of, for example, a storage device such as a semiconductor memory or a magnetic disk. The storage 9 stores, for example, blood vessel running information acquired by the own device or acquired from another device. The storage 9 may also store X-ray images acquired by the image capturing unit 6. In addition, the storage 9 stores various information in the X-ray diagnosis apparatus S.

The operation unit 10 is an example of the operation mechanism that is an interactive interface provided with a keyboard, various switches, a mouse, and the like. A medical worker that uses the X-ray diagnosis apparatus S enters various conditions for imaging such as tube voltage applied to the X-ray tube 11, tube current, and X-ray irradiation time, and a command signal for the start of examination, the movement control of the mechanism unit 5, and the like using the operation unit 10.

The system control circuit C controls the collection and display of X-ray transmission information based on information such as a medical worker's instruction and imaging conditions sent from the operation unit 10, or controls the drive mechanism and the like to control the entire system that forms the X-ray diagnosis apparatus S. The system control circuit C also controls the X-ray diaphragm 12 to achieve an appropriate region of interest based on the position of a device or the like used when a doctor performs a procedure.

The system control circuit C has a blood vessel running information acquiring function C1, a position specifying function C2, and a diaphragm control function C3.

The blood vessel running information acquiring function C1, the position specifying function C2, and the diaphragm control function C3 of the system control circuit C correspond to the blood vessel running information acquiring unit, the device position specifying unit, and the diaphragm controller in the claims, respectively.

The blood vessel running information acquiring function C1 of the system control circuit C is a function to acquire information on the running of blood vessels based on X-ray images captured by the X-ray diagnosis apparatus S when a doctor performs a procedure, such as the insertion of a catheter, on the subject M. For example, before a doctor performs a procedure as mentioned above using interventional radiology (IVR), the images of the blood vessels of the subject M are captured to acquire blood vessel running information such as shape including the width and branch shape of the blood vessel path and the running direction.

Specifically, for example, contrast agent is injected through an imaging catheter inserted into the blood vessel of the subject M and irradiated with X-rays emitted from the X-ray generator 1. Thereby, contrast X-ray images are captured in time series based on the X-rays detected by the X-ray detector 2. The system control circuit C uses a bottom trace image, which is obtained by assigning the minimum pixel value of each pixel to one of the time-series contrast X-ray images captured by the blood vessel running information acquiring function C1 or each pixel, as an image that illustrates the running of blood vessels. Then, the system control circuit C extracts the core line of the blood vessel path (a curve that connects the approximate centers of blood vessel regions) from the image illustrating the running of blood vessels, and calculates the width of the blood vessel path at each position on the core line. The system control circuit C specifies the branch shape of the blood vessel and the running direction at each position of the blood vessel path based on the core line extracted.

In this manner, the system control circuit C acquires blood vessel running information using the blood vessel running information acquiring function C1. The blood vessel running information is stored, for example, in the storage 9.

Although the blood vessel running information is described as being acquired by the system control circuit C with the blood vessel running information acquiring function C1, the information need not necessarily be acquired by the own device. For example, the information may be acquired from another device than the own device. Examples of "another device" include other X-ray diagnosis apparatuses, X-ray CT systems, and the like. The information may be acquired from another device via, for example, a communication control circuit or a communication network not illustrated in FIG. 1. The blood vessel running information may be a three-dimensional image based on three-dimensional volume data.

The position specifying function C2 of the system control circuit C is a function to specify the position of a device, for example, the tip position in an X-ray image. Not only specifying the current tip position of the device, but the position specifying function C2 also estimates a position where the device is heading or moving in future (movement position).

The system control circuit C estimates the movement position of the tip of the device with the position specifying function C2 based on the tip position of the device and the frame rate in a plurality of frames of X-ray images captured in the past. By using these pieces of information, the system control circuit C can calculate the movement amount of the tip position of the device in future.

With regard to the movement amount of the tip position of the device, for example, difference value in information on the tip position of the device are obtained from successive frames in a plurality of past frames, and the average of the difference value is defined as the movement amount. However, the movement amount need not necessarily be obtained in this manner.

The diaphragm control function C3 of the system control circuit C is a function to control the X-ray diaphragm 12 based on blood vessel running information acquired and the position of the device specified. The diaphragm control function C3 controls the X-ray diaphragm 12 to make the region of interest follow the movement position of the tip of the device so that the region of interest can be set and moved according to the movement position of the tip of the device as described above. It is assumed herein that the region of interest follows the movement position of the tip of the device such that its center is aligned therewith.

The term "region of interest" as used herein refers to a region to be irradiated with X-rays. That is, a region whose X-ray images are to be captured next is set, and the X-ray diaphragm of the X-ray diagnosis apparatus is appropriately controlled such that the region is irradiated with X-rays or high doses of X-rays to restrict the range of X-ray irradiation. Therefore, with the diaphragm control function C3 that controls the X-ray diaphragm 12, the region of interest can be moved to (made follow) the tip position of the device. It is also possible to change the size and shape of the region of interest.

Specifically, first, the system control circuit C acquires information on the tip position of the device specified by the position specifying function C2 using the diaphragm control function C3. The diaphragm control function C3 acquires the movement amount of the tip position of the device calculated by the position specifying function C2. If the movement amount is less than a threshold value set in the advance, the system control circuit C does not control the X-ray diaphragm 12 with the diaphragm control function C3.

This is because, when the movement amount is less than the threshold value, it means that the tip position of the device is currently located in the region of interest, and the movement position of the tip still exists in the region of interest even after the next movement of the device. In this case, it is not necessary to move the region of interest according to the movement position of the tip of the device. Therefore, the system control circuit C does not control the X-ray diaphragm 12 with the diaphragm control function C3.

Note that the threshold value can be set arbitrarily. Further, a plurality of threshold values may be set according to the movement amount of the device. The threshold value may be set based on the actual movement distance of the tip position of the device, or based on the ratio of the movement distance and the distance from the center to the boundary of the region of interest. The threshold value thus set is stored in, for example, the storage 9.

If the threshold value is set as described above, it is not always required to make the region of interest follow the movement position of the tip of the device. The region of interest may also be made always follow the movement position of the tip of the device without this process.

The system control circuit C refers to blood vessel running information at the tip position of the device using the diaphragm control function C3. For example, the system control circuit C checks whether the tip position of the device is located in a thick blood vessel, in a thin blood vessel, or at a branch point of the blood vessel.

When a doctor performs a procedure as moving the device in a blood vessel of the subject M, it is often the case that the device is moved faster so that the movement amount increases in a thick blood vessel than in a thin blood vessel. In general, the movement of the device is slower so that the movement amount decreases in a thin blood vessel since the device is moved more carefully.

Therefore, for example, when the tip position of the device moves from a thick blood vessel to a thin branched blood vessel with the system control circuit C's reference to the blood vessel running information, it is considered that the movement amount of the device is greatly reduced at the branch point.

If the system control circuit C moves the region of interest using the diaphragm control function without referring to the blood vessel running information, the region of interest does not follow the tip position of the device, resulting in that the tip position of the device is not displayed in the region of interest. In order to avoid such a situation, the system control circuit C refers to blood vessel running information and corrects the movement amount of the region of interest as needed.

The system control circuit C can adjust the size and shape of the region of interest using the diaphragm control function C3. For example, in the case where the tip position of the device is entering a branch of a blood vessel, the system control circuit C widens the region of interest with reference to the size of the region of interest when the device moves in a thick blood vessel such that the display 8 displays a range which includes the branch and is larger than the size of the region of interest as a reference.

On the other hand, for example, when the device is moving in a thin blood vessel such as a branch of a blood vessel, if the X-ray diaphragm 12 is controlled to set a very wide area as the region of interest, the subject M is subjected to unnecessary exposure. Therefore, in this case, the size of the region of interest is reduced.

Besides, depending on the tip position of the device, a region other than the blood vessel and the tip position of the device such as, for example, a region outside the blood vessel may be greatly taken in the region of interest. There is no much need to display such a region on the display 8. Therefore, in order to avoid unnecessary exposure for the subject M, the system control circuit C can change the shape of the region of interest to a more suitable shape.

As described above, the system control circuit C controls the X-ray diaphragm 12 with the diaphragm control function C3 after adjusting the movement amount, size, and shape of the region of interest based on blood vessel running information as well as information on the movement position of the tip of the device. The X-ray diaphragm 12 restricts the irradiation range of X-rays emitted from the X-ray tube 11 based on a control signal from the system control circuit C. Thus, the center of the region of interest is overlapped with the tip position of the device.

At the time of examination or treatment, the subject is placed on the bed B. The bed B includes a top plate and a main body (not illustrated in FIG. 1). The top plate is used to place the subject. The main body fixes the bed B to the installation surface and moves the top plate in the horizontal direction or the vertical direction as needed to place the subject at an appropriate position in the treatment.

Figure 2:
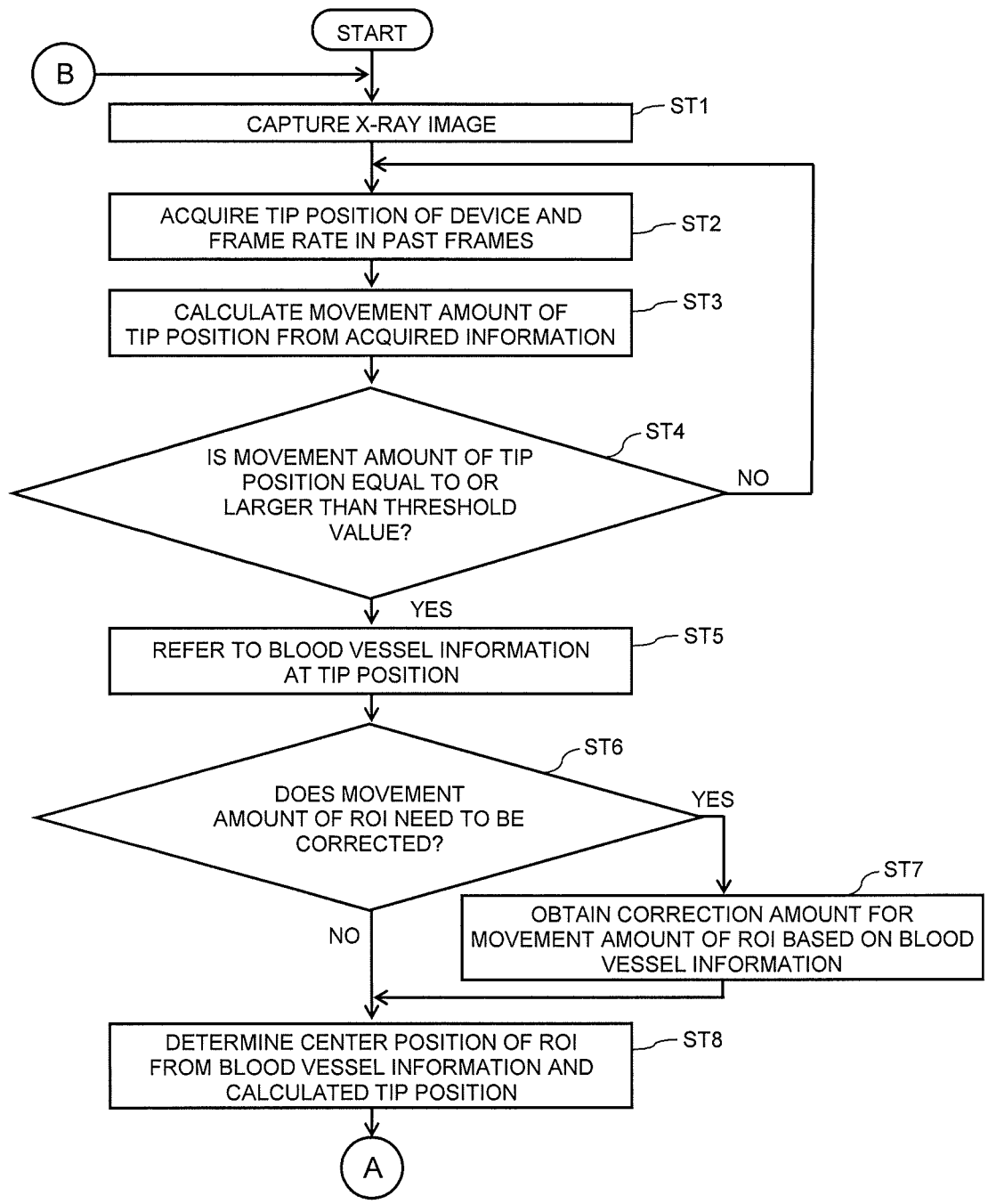
FIG. 2 is a flowchart illustrating the operation of the X-ray diagnosis apparatus of the first embodiment.
Figure 3:
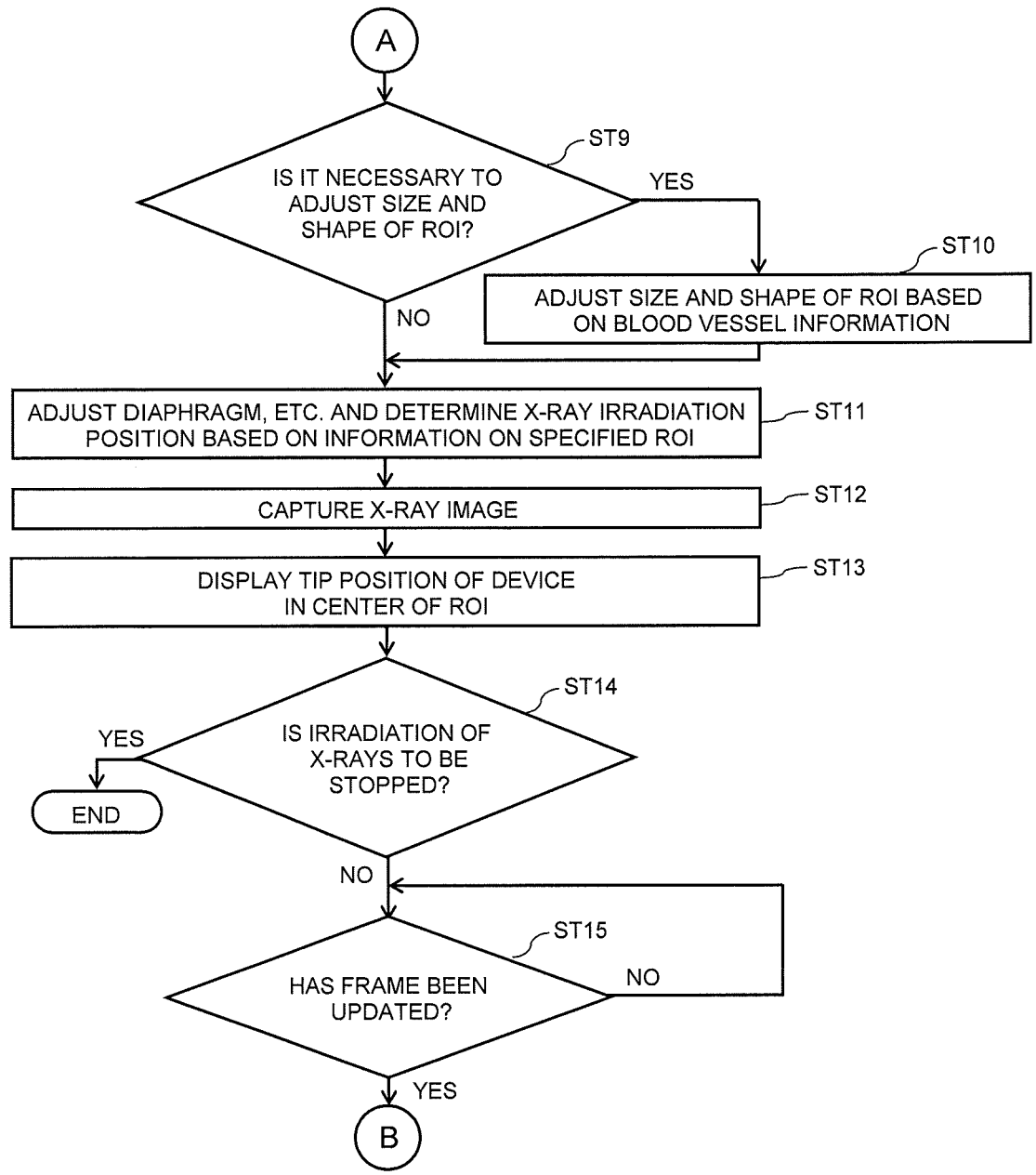
FIG. 3 is a flowchart illustrating the operation of the X-ray diagnosis apparatus of the first embodiment.

The configuration of each part of the X-ray diagnosis apparatus S has been described above. In the following, a description is given of the process of making the region of interest follow the movement of the device with reference to FIGS. 2 to 6. FIGS. 2 and 3 are flowcharts illustrating the operation of the X-ray diagnosis apparatus S according to the first embodiment.

Incidentally, the flowcharts of FIGS. 2 and 3 illustrate the process of making the region of interest follow the movement of the device with respect to one frame of an X-ray image captured. Besides, in the process described below, it is assumed that a doctor has already started a procedure. Accordingly, an X-ray image of one frame has already been captured by the X-ray diagnosis apparatus S and displayed on the display 8. The X-ray image illustrates a device used in the procedure (ST1).

The tip position of the device is displayed in the center of the region of interest. As described above, the region of interest is a region irradiated with X-rays adjusted by the X-ray diaphragm 12 under the control of the diaphragm control function C3 of the system control circuit C.

Figure 4:
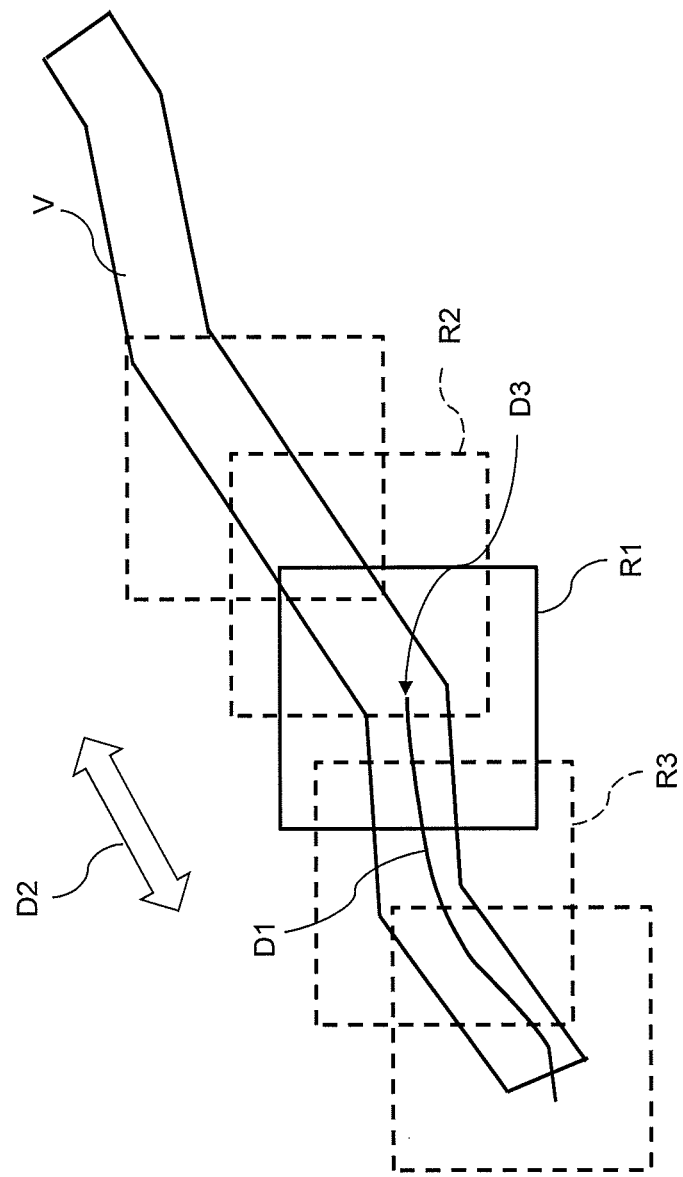
FIG. 4 is a schematic diagram illustrating the relationship between the tip position of a device specified in a blood vessel and a region to be irradiated with X-rays (region of interest) in the X-ray diagnosis apparatus of the first embodiment.

FIG. 4 is a schematic diagram illustrating the relationship between the tip position of a device specified in a blood vessel and the region to be irradiated with X-rays (region of interest) in the X-ray diagnosis apparatus of the first embodiment. FIG. 4 illustrates a blood vessel V in the center. A device D1 is illustrated in the blood vessel V. The device D1 is movable in directions indicated by the large arrow D2. The tip (tip position) of the device D1 is designated by symbol D3.

In FIG. 4, a plurality of rectangles illustrated along the running direction of the blood vessel V each indicate a region of interest. Among them, a region of interest R1 indicated by a solid rectangle in which the tip position D3 of the device D1 is illustrated is a region currently being irradiated with X-rays.

As described above, the region of interest R1 moves along with the movement of the tip position D3 of the device D1. Therefore, in FIG. 4, the past and future movements of the region of interest R1 are indicated by dashed rectangles for better understanding.

First, the system control circuit C specifies the tip position D3 of the device D1 using the position specifying function C2. Specifically, the system control circuit C acquires the tip position D3 of the device D1 and the frame rate in a past frames (ST2). Then, from the information acquired, the position specifying function C2 calculates the movement amount of the tip position D3 in future (ST3).

The system control circuit C uses information on the calculated movement amount of the tip position D3 of the device D1 thus obtained to control the X-ray diaphragm 12 with the diaphragm control function C3. The diaphragm control function C3 determines whether the movement amount of the tip position D3 of the device D1 received is equal to or larger than a threshold value (ST4). That is, it is determined whether it is necessary to move the region of interest R1 following the movement position of the tip position D3.

As a result, if the movement amount of the tip position D3 of the device D1 is less than the threshold value (NO in ST4), the process returns to step ST2, and the system control circuit C acquires the tip position D3 of the device D1 and the frame rate in a past frames again with the position specifying function C2.

On the other hand, when the movement amount of the tip position D3 of the device D1 is equal to or larger than the threshold value (YES in ST4), the system control circuit C refers to blood vessel running information at the current tip position D3 of the device D1 with the diaphragm control function C3 (ST5).

As described above, the blood vessel running information that the system control circuit C refers to is information acquired before the procedure by the doctor. The blood vessel running information may be acquired by the X-ray diagnosis apparatus S or another device. Incidentally, in the flowcharts of FIG. 2 and FIG. 3, "blood vessel running information" is abbreviated as "blood vessel information", and "region of interest" is abbreviated as "ROI".

FIG. 6 is an example of a table in which blood vessel running information is associated with information on the region of interest. The system control circuit C accesses the storage 9 to refer to a table as illustrated in FIG. 6, and determines whether the movement amount of the region of interest needs to be corrected (ST6).

In the example of the table illustrated in FIG. 6, pieces of blood vessel running information are arranged vertically, while pieces of information on the region of interest are arranged horizontally. The blood vessel running information is roughly divided into "diameter" and "branch". As the information on the region of interest (ROI), "movement amount", "size", and "shape" are indicated in this order.

For both the blood vessel running information and the information on the region of interest, the items listed in the table of FIG. 6 are examples only, and information items other than them may be defined in the table.

In the example of the table illustrated in FIG. 6, with respect to the shape of the blood vessel, the diameter (width) "A1" of the blood vessel is associated with the movement amount "X11" of the region of interest. Besides, the branch "B2" is associated with the movement amount "X15" of the region of interest.

With reference to the table as illustrated in FIG. 6, the system control circuit C can determine whether the movement amount of the region of interest needs to be corrected using the diaphragm control function C3 taking the calculated movement amount of the tip position D3 of the device D1 into account.

If the correction is required (YES in ST6), the system control circuit C obtains a correction amount for the movement amount of the region of interest based on the blood vessel running information (ST7). On the other hand, when the correction is not required (NO in ST6), the correction amount is not particularly obtained.

Thus, the system control circuit C has acquired information on the region of interest to be irradiated with X-rays next. That is, the system control circuit C determines the center position of the next region of interest from the blood vessel running information and the tip position D3 of the device D1 calculated using the diaphragm control function C3 (ST8).

In the example of FIG. 4, a region R2 is the region of interest to be irradiated with X-rays next. That is, it is assumed in this example that the tip position D3 of the device D1 travels in the blood vessel V and reaches the region R2. Therefore, by setting the region R2 as the region of interest, the region of interest can be moved to follow the movement of the tip position D3 of the device D1.

While it is assumed herein that the tip position D3 of the device D1 moves forward in the blood vessel V, for example, it may move backward in the blood vessel V as indicated by the arrow D2 and reach a region R3. In this case also, the region of interest R3 can be irradiated with X-rays according to the movement of the tip position D3.

Next, the system control circuit C determines whether it is necessary to adjust the size and shape of the region of interest (ST9 in FIG. 3). The process of adjusting the size and shape of the region of interest is described with also reference to FIG. 5 as appropriate.

Figure 5:
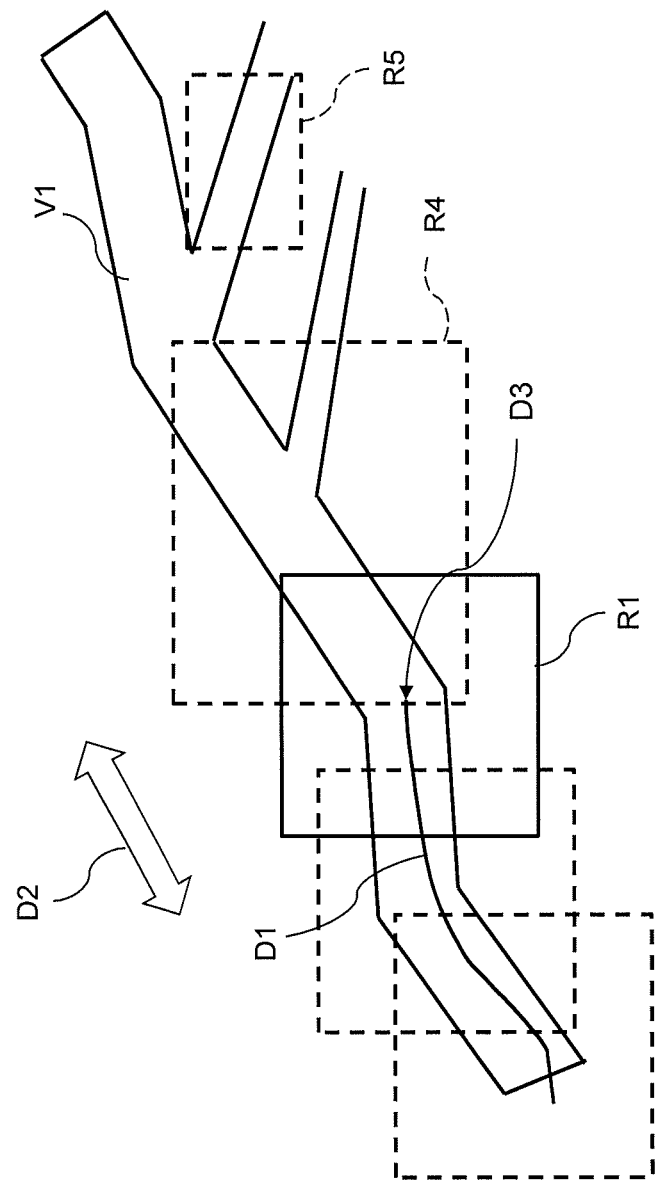
FIG. 5 is a schematic diagram illustrating the relationship between the tip position of a device specified in a blood vessel and a region to be irradiated with X-rays (region of interest) in the X-ray diagnosis apparatus of the first embodiment.

FIG. 5 is a schematic diagram illustrating the relationship between the tip position of a device specified in a blood vessel and a region to be irradiated with X-rays (region of interest) in the X-ray diagnosis apparatus of the first embodiment. FIG. 5 is almost the same as FIG. 4 except for some differences described below.

Blood vessel V1 illustrated in FIG. 5 has a plurality of branches. Differently from FIG. 4, the region of interest illustrated in FIG. 5 is not always indicated by rectangles of the same size. For example, a region of interest R4 adjacent to the region of interest R1 is larger than the region of interest R1. On the other hand, a region of interest R5 adjacent to the region of interest R4 is illustrated smaller than the regions of interest R1 and R4.

For example, when performing an examination or treatment using the device D1, a doctor is likely to move the tip position D3 of the device D1 to any of the branches. Therefore, having found out that there is a branch based especially on the tip position D3 of the device D1 calculated and blood vessel running information using the diaphragm control function C3, the system control circuit C determines whether to adjust the size and shape of the region of interest. This is because, as described above, if the blood vessel has a branch, the size of the region of interest needs to be increased to include the branch for the doctor to perform a procedure.

The system control circuit C refers to the association between the blood vessel running information and information on the region of interest illustrated in FIG. 6. For example, branch "B3" of the blood vessel running information is associated with size "Y16" and shape "Z16" of the region of interest.

The system control circuit C acquires the form of the blood vessel V1 at the newly estimated tip position D3 of the device D1, and compares the size and shape of the region of interest corresponding to the form with the size and shape of the current region of interest. If there is a difference, the system control circuit C determines that the size and shape of the region of interest needs adjustment (YES in ST9).

According to the determination, the system control circuit C adjusts the size and shape of the region of interest, which is a region to be irradiated with X-rays next, based on the association that it has referred to using the diaphragm control function C3 (ST10).

For example, as described above, branch "B3" of blood vessel running information is associated with size "Y16" of the region of interest. Therefore, the system control circuit C sets the size of the region of interest to "Y16" using the diaphragm control function C3, and controls the X-ray diaphragm 12 such that the region of interest thus set is to be irradiated with X-rays. The region to be irradiated with X-rays at this time is represented as, for example, the region of interest R4 in FIG. 5. The system control circuit C adjusts the region of interest R4 to be larger than the region of interest R1 to include the branch using the diaphragm control function C3.

On the other hand, when the device D1 has passed through the branch and entered a thin blood vessel, there is no branch. In this case, the system control circuit C refers to the width (diameter) of the blood vessel V1. In FIG. 5, the region of interest R5 is illustrated smaller than the regions of interest R1 and R4. This is because, when the device D1 moves in a thin blood vessel, the movement amount of the tip position D3 is likely to decrease.

Accordingly, the system control circuit C determines that it is necessary to adjust the size and shape of the region of interest as described above, and adjusts the size and shape of the region of interest, which is a region to be irradiated with X-rays next, based on the association that it has referred to. In this case, the size of the region of interest R5 is also adjusted to be smaller in consideration of the exposure dose of the subject M.

If it is determined that adjustment is not required with reference to the association (NO in ST9), the size and shape of the region of interest is not adjusted.

Thus, the size and shape of the region of interest are specified according to the next tip position D3 of the device D1. The system control circuit C determines an X-ray irradiation position on the subject M based on information on the region of interest specified using the diaphragm control function C3 (ST11). Then, the system control circuit C provides the X-ray diaphragm 12 with an instruction as to irradiation. Thereby, a new X-ray image is captured (ST12).

The display controller 7 displays the X-ray image on the display 8 such that the tip position D3 of the device D1 is aligned with the center of the region of interest, which is a region irradiated with X-rays. Accordingly, the display 8 displays, for example, the tip position D3 of the device D1 in the region of interest R2 as illustrated in FIG. 4 or in the region of interest R5 as illustrated in FIG. 5 (ST13).

The system control circuit C determines whether to continue the irradiation of X-rays onto the region of interest, i.e., whether to stop the irradiation of X-rays onto the region of interest (ST14). Having received a signal indicating to stop the irradiation of X-rays from the operation unit 10 (YES in ST14), the process of making the region of interest follow the movement of the tip position D3 of the device D1 described above ends.

On the other hand, having received a signal indicating to continue the irradiation of X-rays onto the region of interest (NO in ST14), the system control circuit C further determines whether the frame of the X-ray image has been updated, i.e., whether a new X-ray image has been captured (ST15). If a new X-ray image has not been captured (NO in ST15), the display 8 keeps displaying the same image.

On the other hand, when the frame has been updated (YES in ST15), the process returns to step ST1, and the system control circuit C repeats the process of making the region of interest follow the movement of the tip position D3 of the device D1.

In this manner, the system control circuit C estimates the next tip position of the device currently displayed on the display, and controls the X-ray diaphragm 12 such that the region of interest includes the tip position of the device. Thereby, the region of interest can be set and moved according to the movement of the tip position of the device.

That is, the X-ray diagnosis apparatus is used to capture X-ray images of a subject while a doctor performs a procedure such as, for example, the insertion of a catheter into the subject. At this time, the doctor proceeds with the procedure while viewing the captured X-ray images to check the internal structure of the subject.

On this occasion, if all possible regions are irradiated with X-rays to capture X-ray images, the subject may be forced to receive excessive exposure. Therefore, a region whose X-ray images are to be captured is set, and the X-ray diaphragm of the X-ray diagnosis apparatus is appropriately controlled such that the region is irradiated with X-rays or high doses of X-rays to restrict the range of X-ray irradiation. The region irradiated with X-rays thus set is a "region of interest" where the doctor performs a procedure.

Then, the doctor appropriately displays an X-ray image captured by X-ray irradiation on the entire region according to the progress of the procedure. Since the device moves in a blood vessel according to the progress of the procedure, it is necessary to make the region of interest follow the movement of the device. In conventional methods, the operation of setting the region of interest to restrict the region irradiated with X-rays is performed with respect to each region of interest, and therefore the region of interest is reset each time the device moves.

For example, a medical worker such as a technician manually resets the region of interest according to the procedure of the doctor. The region of interest may be automatically made follow the movement of the device by estimating the movement vector of the device.

However, in the method in which the region of interest is automatically made follow the movement of the device, for example, if the device suddenly changes the direction of its movement, it is difficult to make the region of interest follow the movement. In addition, for example, when a doctor repeatedly moves the device back and forth to insert the device into the blood vessel, similarly, it is difficult to make the region of interest follow the back and forth movement of the device.

Besides, when the region of interest is made follow the movement of the device by using the movement vector of the device, if images are captured at a low frame rate, there are only a few base X-ray images, resulting in less accuracy in the estimation of the movement vector. As accuracy in the estimation of the movement vector decreases, it becomes difficult to make the region of interest follow the movement of the device.

Further, from the viewpoint of reducing exposure of a subject, it is preferable that the size of the region of interest can be changed by adjusting the diaphragm appropriately according to the movement of the device.

Therefore, by performing the process as described above, at least one of the X-ray diaphragm and the X-ray filter can be appropriately controlled. That is, the efficiency of the procedure and safety can be improved by simply controlling the X-ray irradiation diaphragm or filter according to the movement of the device and setting an appropriate irradiation range. Thereby, it is possible to reduce the exposure dose of the subject and medical workers.

Although steps ST1 to ST15 have been described as a series of processes, for example, when it is clear that the blood vessel has no branch, steps ST1 to ST8 may be repeated. With this, the system control circuit C controls the X-ray diaphragm 12 with the diaphragm control function C3 such that the region of interest moves following the tip position of the device. Thereby, a region irradiated with X-rays can be moved.

A description has been given of the process in which the diaphragm control function controls the X-ray diaphragm to restrict a region to be irradiated with X-rays, thereby moving the region of interest according to the movement of the tip position of the device. In this process, when a region of interest is created, a filter may be used to restrict a region to be irradiated with X-rays. That is, by moving the filter according to the movement of the tip position of the device, the region of interest can be made to follow the movement of the tip position of the device.

In this case, the filter is arranged between the X-ray tube and the subject, and attenuates X-rays emitted to the site where exposure is to be reduced. The filter includes, for example, a plurality of independently movable metal plates, each made of such material as, for example, a copper plate, aluminum, or the like. The material is not limited to a copper plate or aluminum, and any material can be used as long as it can attenuate X-rays. Each of the metal plates has, for example, a rectangular shape. The number of the metal plates constituting the filter can be set arbitrarily.

The filter may be formed of a plurality of independently movable metal plates as described above, or, for example, a single metal plate having an opening.

The filter is rotated or horizontally moved through a filter drive mechanism under the control of the filter drive control function of the system control circuit. That is, the filter drive mechanism rotates or horizontally moves one or a plurality of metal plates to reduce X-rays generated by the X-ray tube such that the subject is irradiated with less X-rays.

Second Embodiment

In the following, a second embodiment is described in detail with reference to FIGS. 7 to 10.

Figure 7:
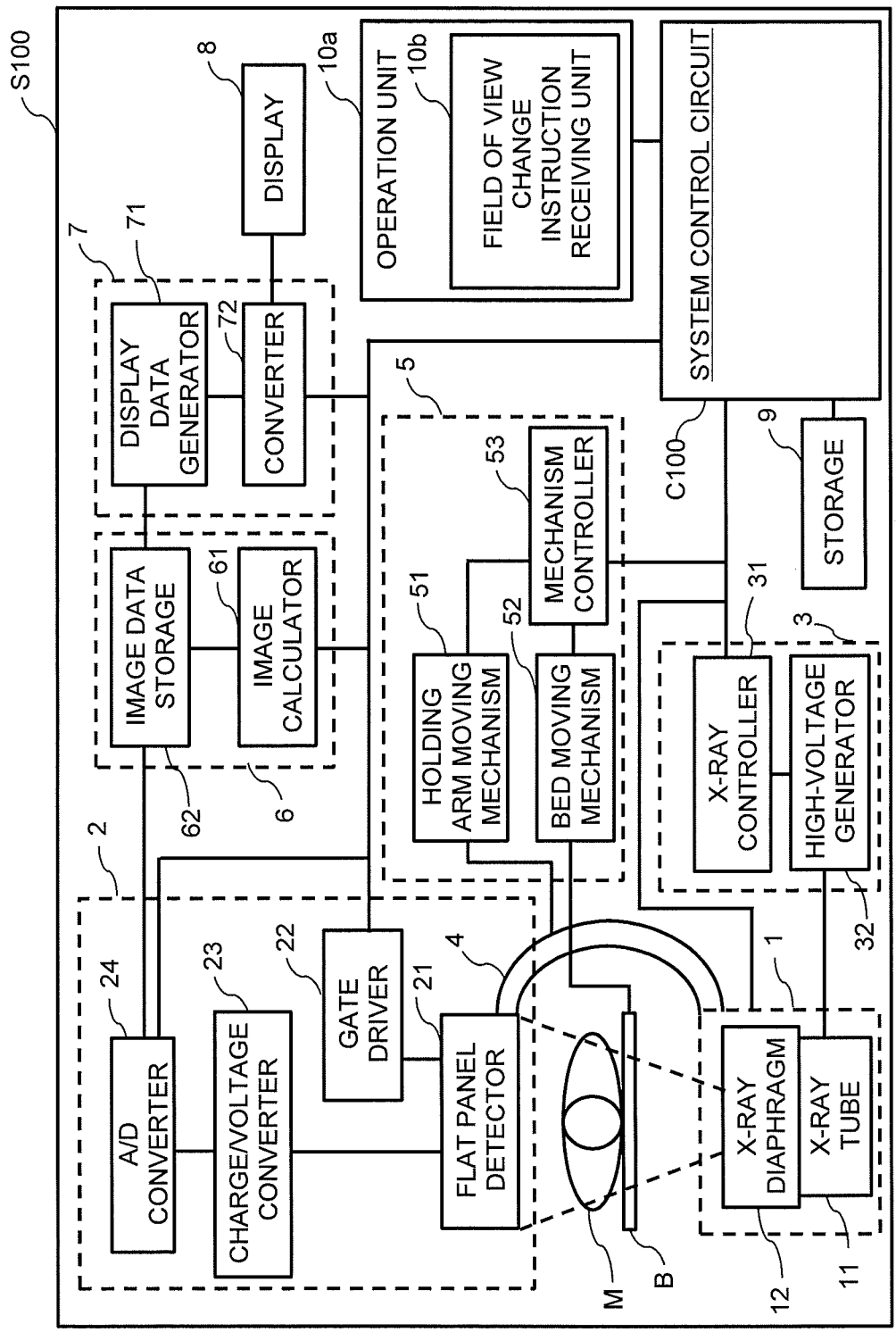
FIG. 7 is a block diagram illustrating the configuration of an X-ray diagnosis apparatus according to a second embodiment.
Figure 8:
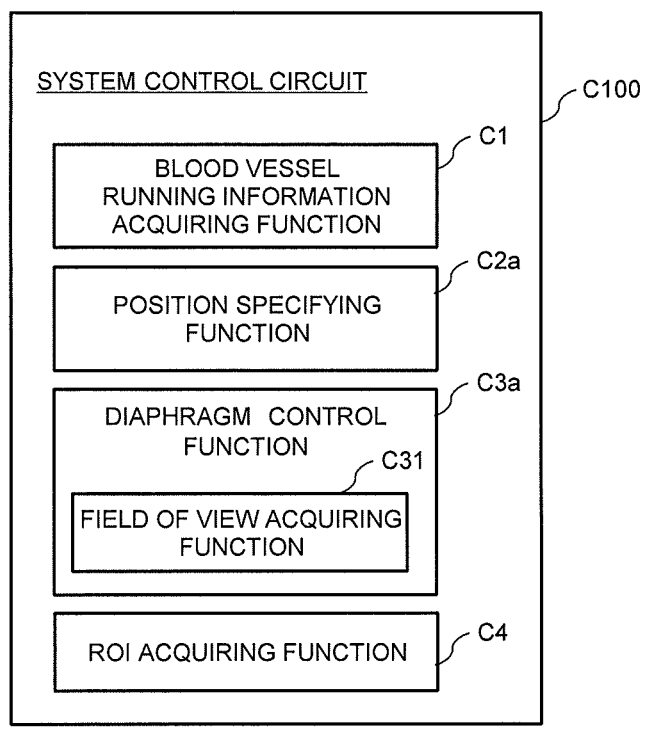
FIG. 8 is a block diagram illustrating the configuration of a system control circuit of the second embodiment.
Figure 9:
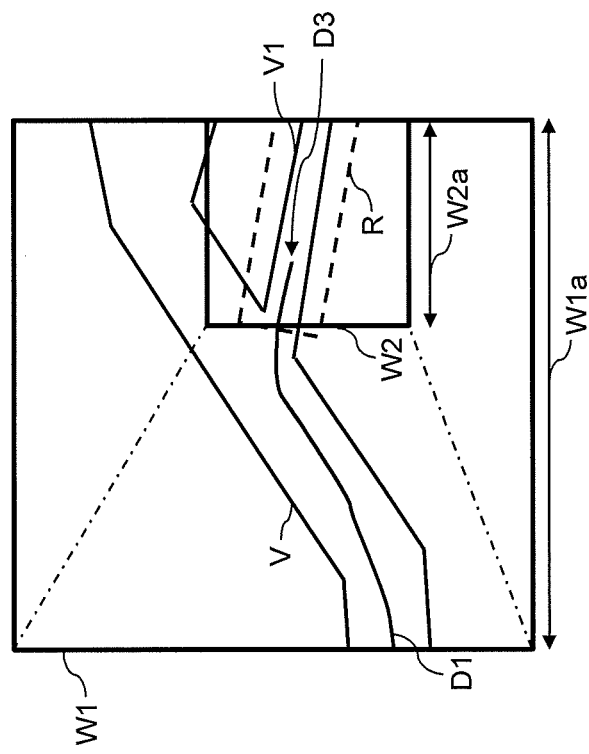
FIG. 9 is a schematic diagram illustrating the relationship between the field of view and a region of interest.
Figure 10:
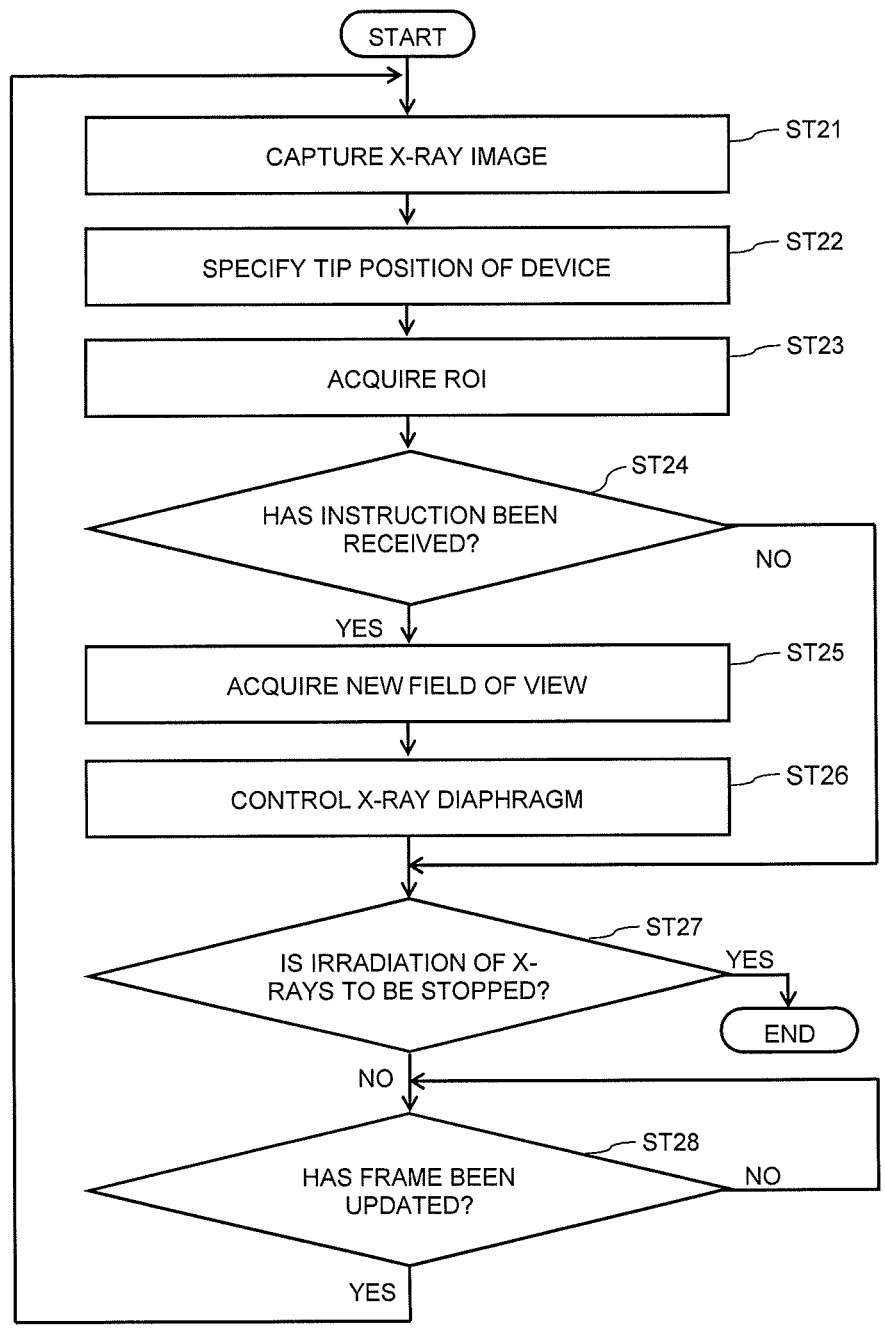
FIG. 10 is a flowchart illustrating the operation of the X-ray diagnosis apparatus of the second embodiment.

FIG. 7 is a block diagram illustrating the configuration of an X-ray diagnosis apparatus S100 according to the second embodiment. FIG. 8 is a block diagram illustrating the configuration of a system control circuit C100 of the second embodiment. FIG. 9 is a schematic diagram illustrating the relationship between the field of view and a region of interest. FIG. 10 is a flowchart illustrating the operation of the X-ray diagnosis apparatus S100 of the second embodiment.

As illustrated in FIG. 7, the X-ray diagnosis apparatus S100 of the second embodiment is basically similar to the X-ray diagnosis apparatus S of the first embodiment except an operation unit 10a and the system control circuit C100. Like reference numerals or symbols are used to designate like elements as those in the first embodiment, and the same description is not repeated.

As illustrated in FIG. 7, the operation unit 10a of the second embodiment includes a field of view change instruction receiving unit 10b. The operation unit 10a and the field of view change instruction receiving unit 10b are examples of the operation mechanism and the field of view change instruction receiving mechanism that are interactive interfaces provided with buttons, a keyboard, various switches, a mouse, and/or the like. The field of view change instruction receiving unit 10b receives, from a medical worker who uses the X-ray diagnosis apparatus S100, an instruction to change the size of the field of view of an X-ray image displayed on the display 8 to a different size. The instruction to change the size of the field of view to a different size includes an instruction to magnify a part of an X-ray image currently displayed on the display 8, i.e., an instruction to zoom in on the image. The instruction also includes an instruction to display an X-ray image currently displayed on the display 8 in a wider field of view, i.e., an instruction to zoom out on the image. The instruction received through the field of view change instruction receiving unit 10b of the operation unit 10a is sent to the system control circuit C100. The system control circuit C100 determines whether an instruction has been received to change the size of the field of view to a different size.

The size of the field of view includes the area of the field of view, the length of one side of the field of view, the magnification, and the like. Besides, the field of view refers to the range of an X-ray image displayed on the display 8, the range in which X-rays are detected by the flat panel detector 21, or the range of a region irradiated with X-rays formed by the X-ray diaphragm 12. After the change, the field of view has a size according to an instruction to change the size of the field of view to a different size. The size of the field of view before the change may be referred to as "first size", while the size of the field of view after the change, i.e., the size according to the change instruction, may be referred to as "second size". The field of view change instruction receiving unit 10b may include, for example, a zoom-in button and a zoom-out button, a plurality of buttons for designating regions where detection is performed by the flat panel detector 21, such as 7×7 inches and 3×3 inches, and/or a plurality of buttons for designating different magnifications. Alternatively, the field of view change instruction receiving unit 10b may be formed of one button, and the size of the field of view may be sequentially switched to different values by the press of the button. These buttons are presented as examples of the above-mentioned interactive interface.

As illustrated in FIG. 8, the system control circuit C100 of the second embodiment illustrated in FIG. 7 has the blood vessel running information acquiring function C1, a position specifying function C2a, a diaphragm control function C3a, and a region of interest (ROI) acquiring function C4. The diaphragm control function C3a includes a field of view acquiring function C31.

The blood vessel running information acquiring function C1, the position specifying function C2a, the diaphragm control function C3a, and the ROI acquiring function C4 of the system control circuit C100 correspond to the blood vessel running information acquiring unit, the device position specifying unit, the diaphragm controller, and the region of interest acquiring unit in the claims, respectively.

According to the second embodiment, the position specifying function C2a specifies the position (for example, the tip position) of a device in an X-ray image. In this case, the X-ray image refers to the current frame or the latest frame of an X-ray image.

Described below are the diaphragm control function C3a and the ROI acquiring function C4. First, the ROI acquiring function C4 is described. The ROI acquiring function C4 acquires a region of interest (ROI) in an X-ray image. The region of interest is a region where a device and a blood vessel that contains the device are present (for example, a region where the tip of the device and a blood vessel that contains the tip are present). With reference to blood vessel running information already acquired and the position of the device specified by the position specifying function C2a, the ROI acquiring function C4 acquires the region of interest in an X-ray image based on the blood vessel running information and the specified position of the device. For example, with reference to blood vessel running information already acquired and the tip position of the device specified by the position specifying function C2a, the ROI acquiring function C4 acquires the region of interest in an X-ray image based on the blood vessel running information and the tip position of the device. The blood vessel running information is the same as that described in the first embodiment.

Referring to FIG. 9, a region of interest R is illustrated as an example of the region of interest. FIG. 9 illustrates the tip position D3 of the device D1, the blood vessel V, and the blood vessel V1 that is a part of the blood vessel V. In FIG. 9, the tip position D3 of the device is located in the blood vessel V1. The region of interest R, illustrated in dashed lines, is set to include the tip position D3 of the device and a blood vessel that contains the tip position D3, i.e., the blood vessel V1. For example, the region of interest R is set along the blood vessel V1 as illustrated in FIG. 9. That is, the region of interest R may be inclined with respect to the field of view W1 (described later) to be along the blood vessel. In the example of FIG. 9, the region of interest R is set such that the region of the blood vessel V1 where the tip position D3 of the device is heading within the region of the interest R is larger than the region of the blood vessel V1 where the tip position D3 has already passed within the region of the interest R; however, the region of interest may be set arbitrarily, as long as it includes at least the tip position D3 of the device and the blood vessel that contains the tip position D3. Besides, in the example of FIG. 9, the region of interest R is illustrated as being rectangular in shape; however, the shape of the region of interest R is not limited to rectangle, and may be square, circular, oval, or the like.

Referring back to FIG. 8, the diaphragm control function C3a and the field of view acquiring function C31 of the diaphragm control function C3a are described.

When the field of view change instruction receiving unit 10b receives an instruction to change the size of the field of view to a different size, the field of view acquiring function C31 acquires a part of the region of an X-ray image as a new field of view having a size according to the instruction based on the size according to the instruction and a region of interest acquired. More specifically, the field of view acquiring function C31 acquires a part of the region of an X-ray image as a new field of view having a size according to the instruction such that the new field of view includes the region of interest. When the new field of view includes the region of interest, it means that the region of interest is completely included in the new field of view or that the region of interest is included in the changed field of view to the fullest extent.

Then, the diaphragm control function C3a controls the X-ray diaphragm 12 based on the new field of view. Specifically, the diaphragm control function C3a controls the X-ray diaphragm 12 to set the new field of view having a size according to the instruction as a region to be irradiated with X-rays. The display 8 displays an X-ray image corresponding to the new irradiation region.

FIG. 9 illustrates the region of interest R and the blood vessels V and V1, the field of view W1 before a change, and the field of view W2 after the change. With reference to FIG. 9, zoom-in operation is described below as an example. In this example, the size of one side of the field of view is specified to change the size of the field of view. The size W2a of one side of the field of view W2 after the change is less than the size W1a of one side of the field of view W1 before the change. It is assumed in this example that a medical worker provides an instruction to change the size of the field of view to the size W2a while the display 8 displays an X-ray image in the field of view W1 before the change. The field of view acquiring function C31 acquires a part of the region of the X-ray image as the new field of view W2 having the size W2a based on the instructed size W2a of the field of view and the region of interest R acquired such that the region of interest R is included in the changed field of view W2 to the fullest extent. An X-ray image corresponding to the field of view W2 after the change is displayed on the display 8 in the same size as the X-ray image corresponding to the field of view W1 before the change, resulting in a zoomed-in view.

The configuration of the X-ray diagnosis apparatus S100 has been described above. In the following, the process of changing the field of view is described with reference to FIG. 10. In FIG. 10, steps ST27 and ST28 are the same as steps ST14 and ST15 described in the first embodiment, and therefore they are not described in detail. The zoom-in operation is described below as an example.

In the flowchart of FIG. 10, the system control circuit C100 of the X-ray diagnosis apparatus S100 first instructs to capture an X-ray image, and an X-ray image is captured (ST21). The system control circuit C100 specifies the tip position of the device in the X-ray image using the position specifying function C2a (ST22). Then, the system control circuit C100 acquires a region of interest (ROI) based on blood vessel running information and the specified tip position using the ROI acquiring function C4 (ST23).

Then, system control circuit C100 determines whether an instruction has been received to change the size of the field of view to a different size (ST24). If it is determined that an instruction has been received (YES in ST24), the process proceeds to step ST25. The system control circuit C100 acquires a new field of view based on a size according to the instruction and the region of interest using the field of view acquiring function C31 (ST25). Specifically, the field of view acquiring function C31 acquires a part of the region of the X-ray image as a new field of view having a size according to the instruction such that the new field of view includes the region of interest.

Next, the system control circuit C100 controls the X-ray diaphragm 12 based on the new field of view using the diaphragm control function C3a (ST26). Specifically, the diaphragm control function C3a controls the X-ray diaphragm 12 to set the new field of view having a size according to the instruction as a region irradiated with X-rays. The display 8 displays an X-ray image corresponding to the new irradiation region.

On the other hand, when the system control circuit C100 determines that an instruction has not been received to change the size of the field of view to a different size (NO in ST24), the process proceeds to step ST27. A description has been given above of the process of changing the field of view.

Steps ST21 to ST28 have been described as a series of processes; however, for example, steps relating to the acquisition of a region of interest and steps relating to the process based on the acquired region of interest may be independently performed.

As described above, according to the second embodiment, a region of interest is acquired based on blood vessel running information and the tip position of the device specified. With this, the region of interest can be set to a region that a medical worker focuses on. When the size of the field of view is changed, the position of the field of view after the change is determined based on the acquired region of interest. This eliminates the need for a medical worker to move the holding arm 4 or the bed B after entry of an instruction to change the size of the field of view so that the field of view after the change includes the region of interest. Further, the method of setting a region of interest is simplified and the position of the region of interest is optimized, whereby the procedure efficiency and the treatment safety are improved.

In the second embodiment described above, when an instruction is received to change the size of the field of view to a different size, a new field of view is acquired based on the size according to the instruction and a region of interest acquired. Although the new field of view is described as being set so as to include the region of interest, this is by way of example only. For example, the new field of view may be set such that the center thereof after zooming-in is close to the center of the region of interest. When the new field of view is set such that its center after zooming-in is close to the center of the region of interest, the region of interest may not be included in the new field of view to the fullest extent. However, the field of view can be set in consideration of blood vessel running information as well as the position of the tip of the device.

Modification of Second Embodiment

Figure 11:
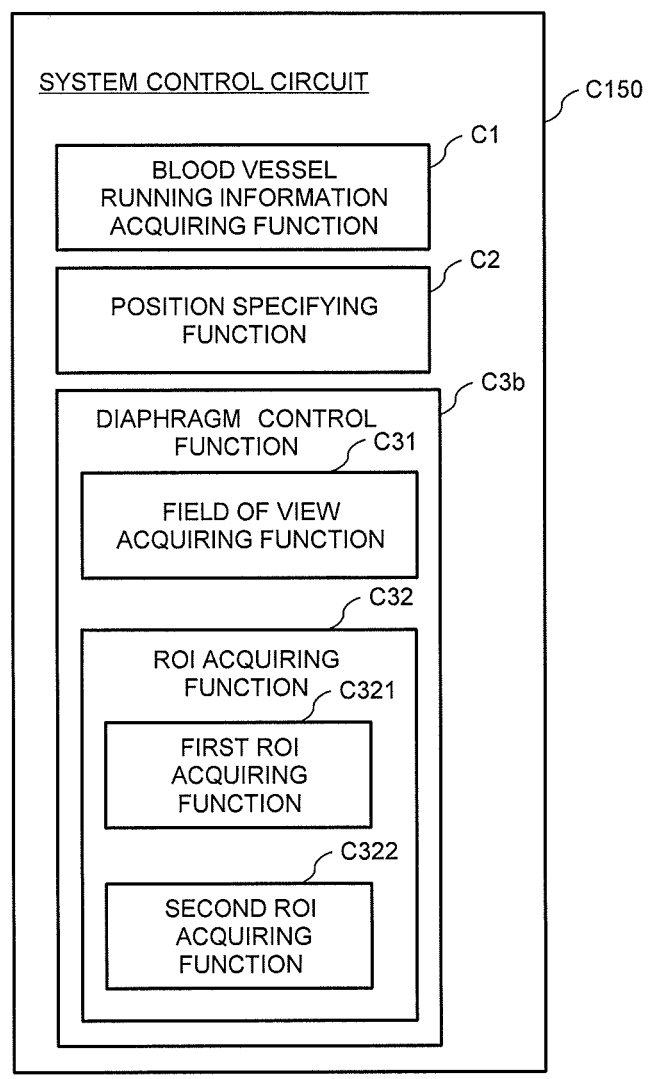
FIG. 11 is a block diagram illustrating the configuration of a system control circuit according to a modification of the second embodiment.

In the following, a modification of the second embodiment is described in detail with reference to FIG. 11. FIG. 11 is a block diagram illustrating the configuration of a system control circuit C150 according to a modification of the second embodiment. This modification of the second embodiment corresponds to a combination of the first embodiment and the second embodiment. The X-ray diagnosis apparatus S100 according to the modification of the second embodiment includes a system control circuit C150 instead of the system control circuit C100 illustrated in FIG. 7. Like reference numerals or symbols are used to designate like elements as those in the first and second embodiments, and the same description is not repeated.

As illustrated in FIG. 11, the system control circuit C150 has the blood vessel running information acquiring function C1, the position specifying function C2, and a diaphragm control function C3b. The diaphragm control function C3b includes the field of view acquiring function C31 and a ROI acquiring function C32. The ROI acquiring function C32 includes a first ROI acquiring function C321 and a second ROI acquiring function C322.

The blood vessel running information acquiring function C1, the position specifying function C2, the diaphragm control function C3b, and the ROI acquiring function C32 of the system control circuit C150 correspond to the blood vessel running information acquiring unit, the device position specifying unit, the diaphragm controller, and the region of interest acquiring unit in the claims, respectively.

The first ROI acquiring function C321 is used to perform the process for setting a region of interest described in the first embodiment. The first ROI acquiring function C321 is used to perform steps ST4 to ST10 of the process described in the first embodiment with reference to FIGS. 2 and 3. In the first embodiment, the region of interest is set based on blood vessel running information and a position where the device is heading or moving in future (movement position). The movement position of the device (for example, the movement position of the tip of the device) is estimated based on the position of the device (for example, the tip position of the device) in a plurality of X-ray images. It means that the first ROI acquiring function C321 acquires a region of interest in an X-ray image based on blood vessel running information and the position of the device (for example, the tip position of the device) in the X-ray image. The diaphragm control function C3b controls the X-ray diaphragm 12 based on the region of interest acquired by the first ROI acquiring function C321. Specifically, the diaphragm control function C3b controls the X-ray diaphragm to set the region of interest acquired by the first ROI acquiring function C321 as a region to be irradiated with X-rays.

The second ROI acquiring function C322 is the same function as the ROI acquiring function C4 of the second embodiment. The field of view acquiring function C31 acquires a new field of view based on a size according to an instruction and the region of interest acquired by the second ROI acquiring function C322. The diaphragm control function C3b controls the X-ray diaphragm 12 based on the new field of view. More specifically, the diaphragm control function C3b controls the X-ray diaphragm 12 to set the new field of view acquired by the field of view acquiring function C31 as a region to be irradiated with X-rays.

Since the new field of view includes the region of interest, it can be said that the new field of view is acquired based on the region of interest. Accordingly, it can also be said that the diaphragm control function C3b controls the X-ray diaphragm 12 based on the region of interest acquired by the second ROI acquiring function C322. The diaphragm control function C3b controls the X-ray diaphragm 12 to set a region that includes the region of interest acquired by the second ROI acquiring function C322, as a region irradiated with X-rays.

Although the ROI acquiring function C32 of the modification of the second embodiment is described herein as being included in the diaphragm control function C3b, it may be parallel to the diaphragm control function C3b as in the second embodiment.

As described above, the modification of the second embodiment corresponds to a combination of the first embodiment and the second embodiment. When an instruction is provided to change the size of the field of view while the display 8 displays an X-ray image in a field of view (a region irradiated with X-rays) followed as in the first embodiment, first, the second ROI acquiring function C322 acquires a region of interest in the field of view displayed on the display 8. Then, the field of view acquiring function C31 acquires a new field of view so as to include the region of interest acquired by the second ROI acquiring function C322. With this, the effects of first embodiment can be combined with the effects of the second embodiment. Thus, the method of setting a region of interest is simplified and the position of the region of interest is optimized, whereby the procedure efficiency and the treatment safety are improved.

Third Embodiment

In the following, a third embodiment is described in detail with reference to FIGS. 12 to 15.

Figure 12:
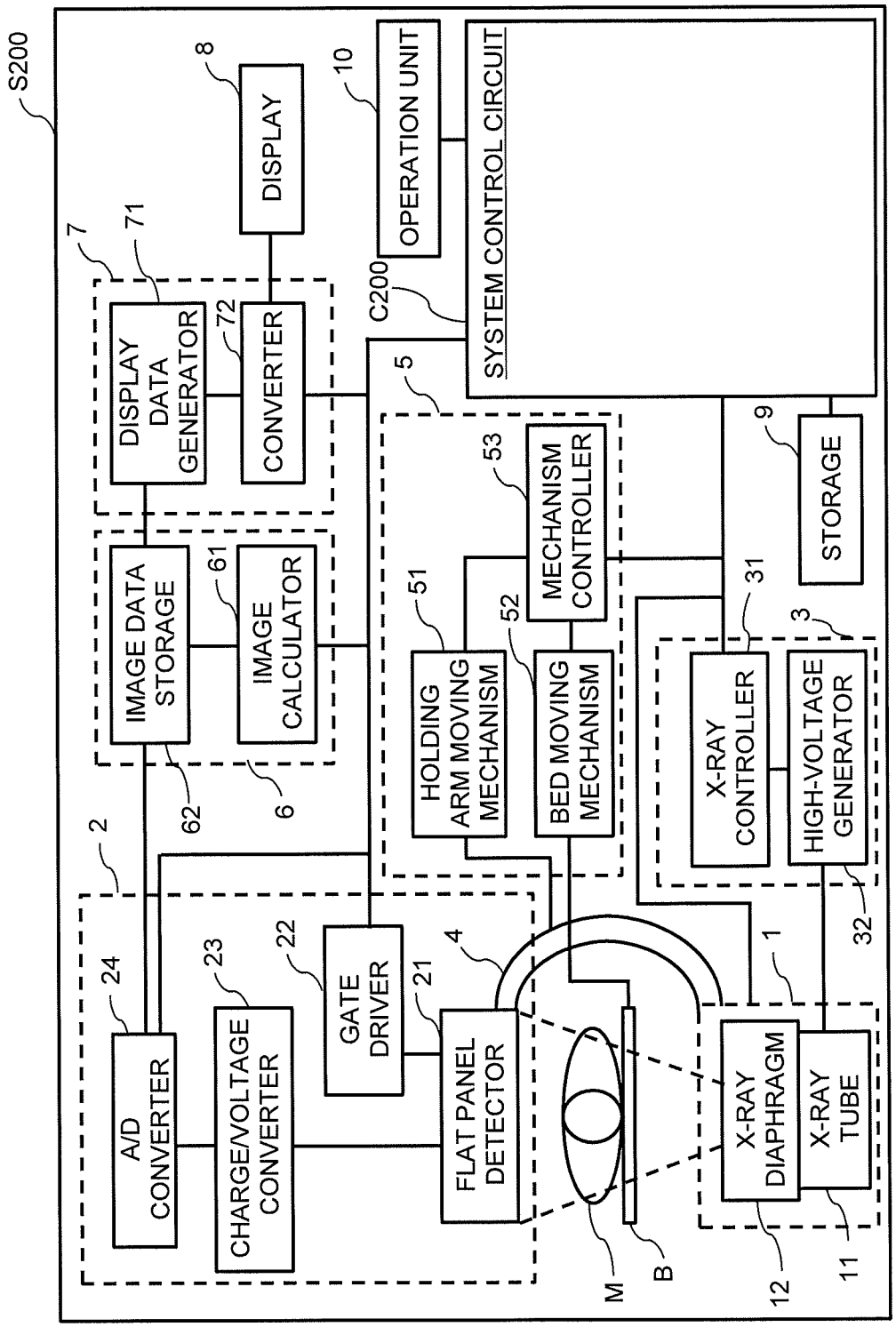
FIG. 12 is a block diagram illustrating the configuration of an X-ray diagnosis apparatus according to a third embodiment.
Figure 13:
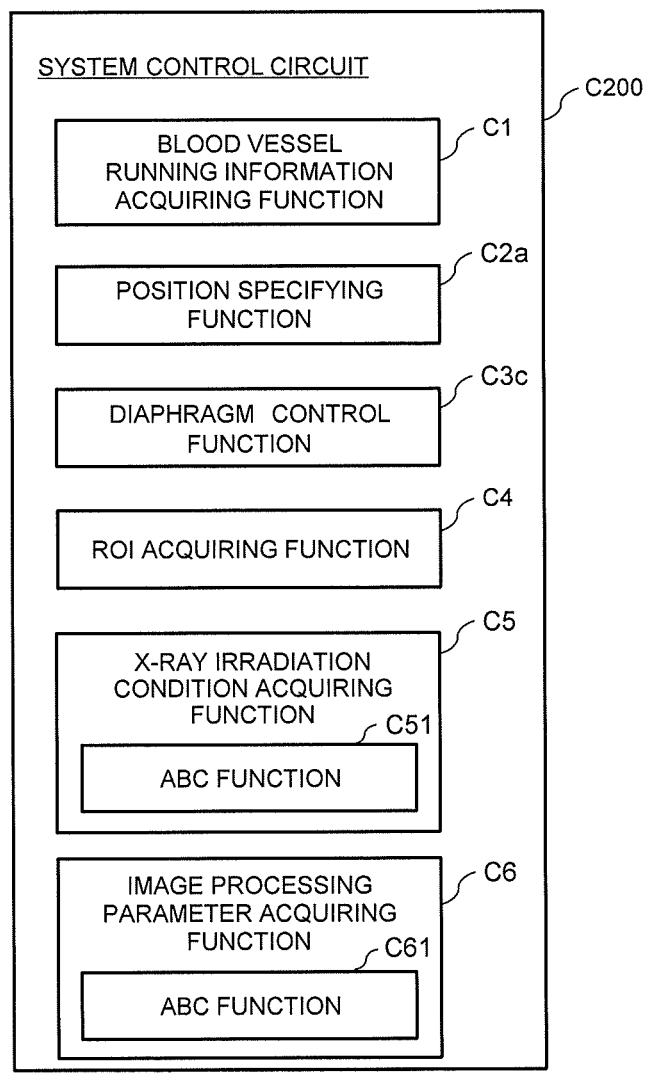
FIG. 13 is a block diagram illustrating the configuration of a system control circuit of the third embodiment.
Figure 14:
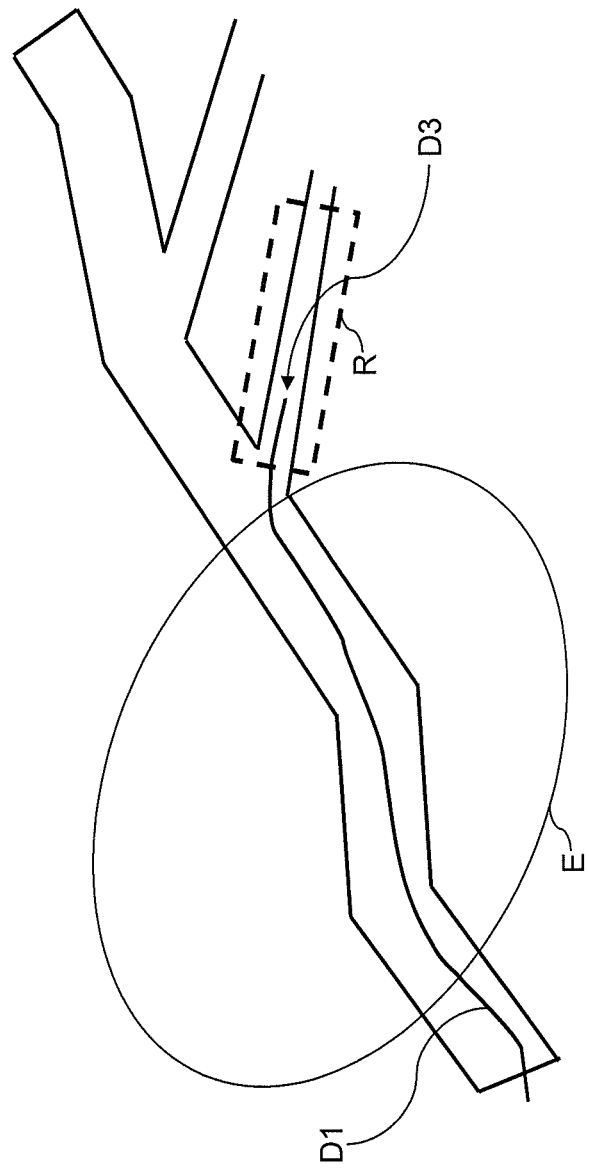
FIG. 14 is a schematic diagram illustrating a region of interest in an X-ray image.
Figure 15:
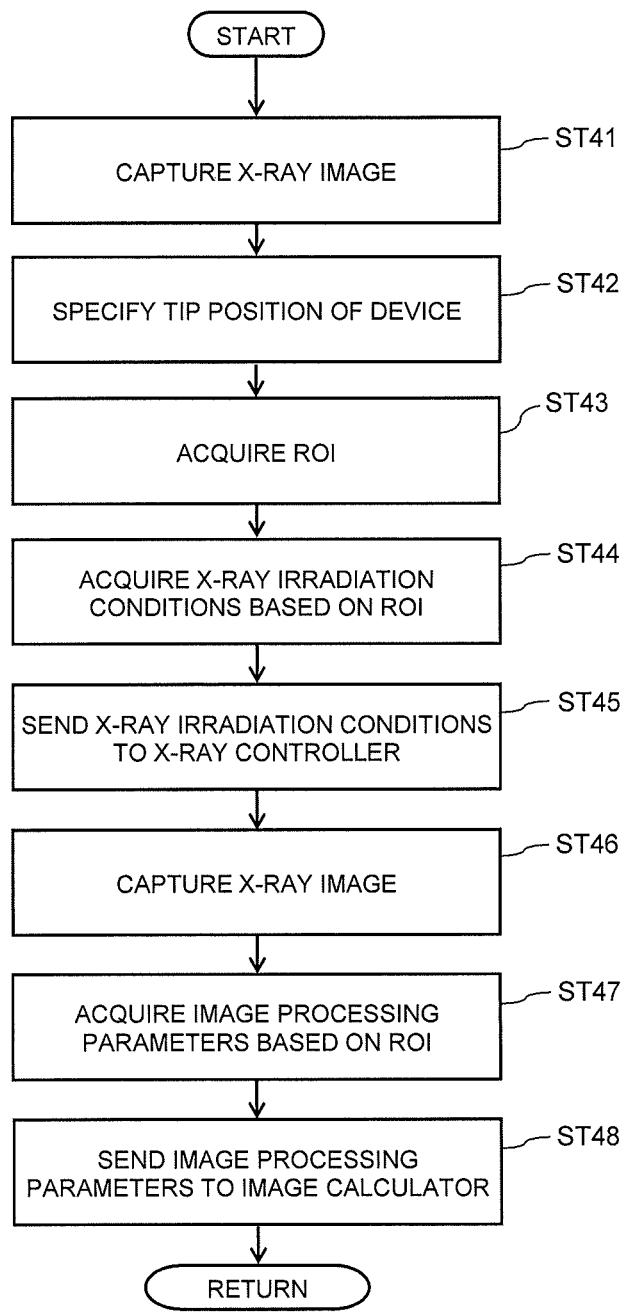
FIG. 15 is a flowchart illustrating the operation of the X-ray diagnosis apparatus of the third embodiment.

FIG. 12 is a block diagram illustrating the configuration of an X-ray diagnosis apparatus S200 according to the third embodiment. FIG. 13 is a block diagram illustrating the configuration of a system control circuit C200 of the third embodiment. FIG. 14 is a schematic diagram illustrating a region of interest in an X-ray image. FIG. 15 is a flowchart illustrating the operation of the X-ray diagnosis apparatus S200 of the third embodiment.

As illustrated in FIG. 12, the X-ray diagnosis apparatus S200 of the third embodiment is basically similar to the X-ray diagnosis apparatus S of the first embodiment and the X-ray diagnosis apparatus S100 of the second embodiment except the system control circuit C200. Like reference numerals or symbols are used to designate like elements as those in the first and second embodiments, and the same description is not repeated.

As illustrated in FIG. 13, the system control circuit C200 has the blood vessel running information acquiring function C1, the position specifying function C2a, the diaphragm control function C3c, the ROI acquiring function C4, an X-ray irradiation condition acquiring function C5, and an image processing parameter acquiring function C6. The X-ray irradiation condition acquiring function C5 includes an ABC function C51. The image processing parameter acquiring function C6 includes an ABC function C61. "ABC" stands for Auto Brightness Control.

The blood vessel running information acquiring function C1, the position specifying function C2a, the diaphragm control function C3c, the ROI acquiring function C4, the X-ray irradiation condition acquiring function C5, and the image processing parameter acquiring function C6 of the system control circuit C200 correspond to the blood vessel running information acquiring unit, the device position specifying unit, the diaphragm controller, the region of interest acquiring unit, the X-ray irradiation condition acquiring unit, and the image processing parameter acquiring unit in the claims, respectively.

The diaphragm control function C3c controls the X-ray diaphragm 12. The ROI acquiring function C4 acquires a region of interest in the same manner as the ROI acquiring function C4 of the second embodiment.

The X-ray irradiation condition acquiring function C5 acquires X-ray irradiation conditions based on the region of interest on an X-ray image acquired by the ROI acquiring function C4. The system control circuit C200 sends the acquired X-ray irradiation conditions to the X-ray controller 31. The X-ray image is, for example, a raw image. The X-ray controller 31 outputs a control signal for X-ray irradiation conditions such as tube current, tube voltage, and irradiation time in the X-ray tube 11 to the high-voltage generator 32 based on the X-ray irradiation conditions received from the system control circuit C200. With this, X-rays are emitted based on the updated X-ray irradiation conditions in subsequent frames (for example, the next frame).

The ABC function C51 of the X-ray irradiation condition acquiring function C5 includes a function of acquiring parameter(s) for adjusting the brightness of an X-ray image based on the region of interest (for example, pixel values in the region of interest) in the X-ray image acquired by the ROI acquiring function C4. The parameter(s) corresponds at least one of the X-ray irradiation conditions. The system control circuit C200 sends the acquired parameter(s) to the X-ray controller 31. The X-ray controller 31 outputs a control signal to the high-voltage generator 32 based on the parameter(s) received from the system control circuit C200. Accordingly, for example, in an X-ray image to be captured next, the brightness is adjusted with reference to the region of interest. Thereby, an image corresponding to the inside of the region of interest can be clearly viewed. The above-mentioned pixel values in the region of interest refer to the values of pixels that form a portion corresponding to the region of interest in the X-ray image.

The region of interest R illustrated in dashed lines in FIG. 14 is an example of the region of interest according to the third embodiment. According to the third embodiment, the region of interest R is acquired in the same manner as in the second embodiment. In FIG. 14, a region E indicates a relatively dark region in an X-ray image. If parameters for adjusting the brightness of the X-ray image are acquired based on the relatively dark region E or a region that includes the relatively dark region E, X-rays are emitted based on X-ray irradiation conditions for brightening the dark region E in subsequent frames (for example, the next frame). This may cause the region of interest R to be too bright.

The ABC function C51 acquires parameters for adjusting the brightness of the X-ray image with reference to the region of interest, thus achieving better visibility of a region that the medical worker wants to view.

The image processing parameter acquiring function C6 illustrated in FIG. 13 acquires image processing parameters based on the region of interest (for example, pixel values in the region of interest) in an X-ray image acquired by the ROI acquiring function C4. The system control circuit C200 sends the acquired image processing parameters to the image calculator 61. The image calculator 61 performs image processing operation on the X-ray image for adjusting the brightness, enhancing the contour, improving the S/N ratio, and the like based on the image processing parameters received from the system control circuit C200. In this example, the X-ray image is a raw image, but it may be obtained by processing a raw image. Further, the raw image is assumed to be obtained under X-ray irradiation conditions acquired by the X-ray irradiation condition acquiring function C5; however, it is not so limited.

The ABC function C61 of the image processing parameter acquiring function C6 acquires parameter(s) for brightness adjustment based on the region of interest (for example, pixel values in the region of interest) in the X-ray image acquired by the ROI acquiring function C4. The parameter(s) corresponds at least one of the image processing parameters. The system control circuit C200 sends the acquired parameter(s) to the image calculator 61. The image calculator 61 performs image processing operation on the X-ray image for adjusting the brightness based on the parameter(s) received from the system control circuit C200. The brightness adjustment indicates brightness adjustment in general image processing, i.e., the adjustment of the gain and/or offset, for example. As a result, the brightness of the X-ray image is adjusted with reference to the region of interest. Thereby, an image corresponding to the inside of the region of interest can be clearly viewed.

The ABC function C61 is described with reference to FIG. 14. If parameters for adjusting the brightness of an X-ray image are acquired based on the relatively dark region E or a region that includes the relatively dark region E, brightness adjustment is performed so as to brighten up the dark region E. This may cause the region of interest R to be too bright.

The ABC function C61 acquires parameters for adjusting the brightness of the X-ray image with reference to the region of interest, thus achieving better visibility of a region that the medical worker wants to view.

The configuration of the X-ray diagnosis apparatus S200 has been described above. In the following, the process of acquiring X-ray irradiation conditions and image processing parameters is described with reference to FIG. 15. In FIG. 15, steps ST41, ST42, and ST43 are the same as steps ST21, ST22, and ST23 of FIG. 10, and therefore they are not described below.

The system control circuit C200 of the X-ray diagnosis apparatus S200 acquires X-ray irradiation conditions based on the region of interest using the X-ray irradiation condition acquiring function C5 (ST44). For example, the system control circuit C200 acquires parameters for adjusting the brightness of an X-ray image as the X-ray irradiation conditions using the ABC function C51 of the X-ray irradiation condition acquiring function C5.

The system control circuit C200 sends the acquired X-ray irradiation conditions to the X-ray controller 31 (ST45). The X-ray controller 31 outputs a control signal to the high-voltage generator 32 based on the X-ray irradiation conditions. The X-ray tube 11 emits X-rays based on the updated X-ray irradiation conditions, and the X-ray detector 2 captures a new X-ray image as the next frame (ST46). Then, the process proceeds to the next step.

The image processing parameter acquiring function C6 of the system control circuit C200 acquires image processing parameters based on the region of interest (ST47). For example, the system control circuit C200 acquires image processing parameters for adjusting the brightness of the X-ray image using the ABC function C61 of the image processing parameter acquiring function C6.

The system control circuit C200 sends the acquired image processing parameters to the image calculator 61 (ST48). The image calculator 61 adjusts the brightness of the X-ray image based on the acquired image processing parameters. A description has been given of the process of acquiring X-ray irradiation conditions and image processing parameters is described.

Steps ST41 to ST48 have been described as a series of process; however, for example, steps relating to the acquisition of X-ray irradiation conditions and steps relating to the acquisition of image processing parameters may be independently performed.

Incidentally, the process of FIG. 15 is performed at a predetermined timing. Examples of the predetermined timing include when X-ray irradiation starts or restarts, when the region of interest is made follow the movement position of the tip of the device, when the size of the field of view is changed, and when the next frame is captured.

The process performed by the position specifying function C2a of the third embodiment may be performed by part of the functions of the position specifying function C2 of the first embodiment.

As described above, according to the third embodiment, a region of interest is acquired based on blood vessel running information and the tip position of the device specified. With this, the region of interest can be set to a region that a medical worker focuses on. Then, X-ray irradiation conditions and image processing parameters are acquired based on the region of interest. Thereby, the X-ray irradiation conditions and the image processing parameters are prevented from being acquired based on a region other than the region that a medical worker focuses on. Accordingly, the X-ray irradiation conditions and the image processing parameters are prevented from being acquired based on, for example, the relatively dark region E illustrated in FIG. 4. As a result, the region that a medical worker focuses on can be prevented from becoming too bright. Thus, the method of setting a region of interest is simplified and the position of the region of interest is optimized, whereby the procedure efficiency and the treatment safety are improved.

The blood vessel running information acquiring function (C1), the position specifying function (C2, C2a), the diaphragm control function (C3, C3a, C3b, C3c), the field of view acquiring function (C31), the ROI acquiring function (C4, C32), the first ROI acquiring function (C321), the second ROI acquiring function (C322), the X-ray irradiation condition acquiring function (C5), the image processing parameter acquiring function (C6), the ABC functions (C51, C61) of the system control circuit (C, C100, C150, C200) may be each implemented by a control circuit. Alternatively, the control circuit and the system control circuit (C, C100, C150, C200) may be provided with application software to implement the above functions.

The image calculator 61 and the X-ray controller 31 may be each implemented by a control circuit or the system control circuit (C, C100, C150, C200) may implement the functions of them. Alternatively, the control circuit and the system control circuit (C, C100, C150, C200) may be provided with application software to implement the above functions.

For example, various functions of the system control circuit (C, C100, C150, C200) and the control circuit can be realized by, for example, a computer program that is stored in a predetermined memory, the storage 9, or the like and executed by a processor. The term "processor" as used herein refers to a circuit such as, for example, a dedicated or general central processing unit (CPU), an application specific integrated circuit (ASIC), a programmable logic device such as a simple programmable logic device (SPLD) and a complex programmable logic device (CPLD), a field programmable gate array (FPGA), or the like.

The processor reads out, for example, a program stored in the storage 9 or directly incorporated in the circuit of the processor and executes it, thereby realizing the function. Each processor may be provided with a recording circuit for storing the program. The recording circuit may store, for example, a program corresponding to the functions of the image capturing unit 6 and the X-ray controller 31, and may have the configuration of the storage 9. The storage is formed of a storage device, examples of which include a semiconductor memory such as a general random access memory (RAM) and a magnetic disk such as a hard disk drive (HDD). The system control circuit, the control circuit, and/or the processor is/are example(s) of a processing circuitry.

In the above embodiments, the movement amount is indicated by a vector including the movement direction and the movement distance.

As described above, the method of setting a region of interest is simplified and the position of the region of interest is optimized, whereby the procedure efficiency and the treatment safety are improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus, comprising:

an X-ray generator configured to emit X-rays;

an X-ray diaphragm configured to restrict a region to be irradiated with the X-rays emitted from the X-ray generator;

an X-ray detector configured to detect the X-rays emitted from the X-ray generator; and a processing circuitry configured to:

acquire an X-ray image based on a detection result obtained by the X-ray detector, acquire blood vessel running information, which comprises information about a blood vessel running in a subject, from volume data acquired by another apparatus, specify a position of a device in the X-ray image, and control the X-ray diaphragm based on the blood vessel running information and the position of the device.

2. The X-ray diagnosis apparatus of claim 1, wherein the processing circuitry is further configured to:

control the X-ray diaphragm such that the region to be irradiated with the X-rays moves according to a movement of the device.

3. The X-ray diagnosis apparatus of claim 2, wherein the processing circuitry is further configured to:

control the X-ray diaphragm such that a center of the region to be irradiated with the X-rays is aligned with a position of a tip of the device.

4. The X-ray diagnosis apparatus of claim 2, further comprising:

a storage circuit configured to store the blood vessel running information in an association with information on the region to be irradiated with the X-ray, wherein the processing circuitry is further configured to:
control the X-ray diaphragm with a reference to the association.

5. The X-ray diagnosis apparatus of claim 1, wherein the processing circuitry is further configured to:

specify the position of the device based on a position of a tip of the device, a plurality of frames of the X-ray image, and a frame rate.

6. The X-ray diagnosis apparatus of claim 1, further comprising:

a user interface configured to receive an instruction to change a size of a field of view, wherein the processing circuitry is further configured to:
acquire a region of interest in the X-ray image based on the blood vessel running information and the position of the device, acquire a part of a region of the X-ray image as a new field of view, in response to the instruction, based on the size of the field of view according to the instruction and the region of interest, and control the X-ray diaphragm to set the new field of view as the region to be irradiated with the X-ray.

7. The X-ray diagnosis apparatus of claim 6, wherein the processing circuitry is further configured to:

acquire a new field of view such that the new field of view includes the region of interest.

8. An X-ray diagnosis apparatus, comprising:
an X-ray generator configured to emit X-rays;
a filter located between the X-ray generator and a subject, and having an opening through which the X-rays emitted from the X-ray generator pass;
an X-ray detector configured to detect the X-rays emitted from the X-ray generator; and
a processing circuitry configured to:
acquire an X-ray image based on a detection result obtained by the X-ray detector,
acquire blood vessel running information, which comprises information about a blood vessel running in the subject, from volume data acquired by another apparatus,
specify a position of a device in the X-ray image, and
control the filter based on the blood vessel running information and the position of the device.

9. The X-ray diagnosis apparatus of claim 8, wherein the processing circuitry is further configured to:

control the filter such that the region to be irradiated with the X-rays moves according to a movement of the device.

10. The X-ray diagnosis apparatus of claim 9, wherein the processing circuitry is further configured to:

control the filter such that a center of the region to be irradiated with the X-rays is aligned with a position of a tip of the device.

11. The X-ray diagnosis apparatus of claim 9, further comprising:

a storage circuit configured to store the blood vessel running information in an association with information on the region irradiated with the X-rays, wherein the processing circuitry is further configured to:
control the filter with a reference to the association.

12. The X-ray diagnosis apparatus of claim 8, wherein the processing circuitry is further configured to:

specify the position of the device based on a position of a tip of the device, a plurality of frames of the X-ray image, and a frame rate.

13. An X-ray diagnosis apparatus, comprising:
an X-ray generator configured to emit X-rays;
an X-ray detector configured to detect the X-rays emitted from the X-ray generator;
a user interface configured to receive an instruction to change a size of a field of view; and
a processing circuitry configured to:
acquire an X-ray image based on a detection result obtained by the X-ray detector,
acquire blood vessel running information, which comprises information about a blood vessel miming in a subject,
specify a position of a device in the X-ray image,
acquire a region of interest in the X-ray image based on the blood vessel running information and the position of the device,
acquire a part of a region of the X-ray image as a new field of view, in response to the instruction, based on the size of the field of view according to the instruction and the region of interest, and
control an X-ray diaphragm to set the new field of view as the region to be irradiated with the X-rays.

14. The X-ray diagnosis apparatus of claim 13, wherein the processing circuitry is further configured to:

acquire an X-ray irradiation condition using the region of interest.

15. The X-ray diagnosis apparatus of claim 14, wherein the processing circuitry is further configured to:

acquire the X-ray irradiation condition based on a pixel value in the region of interest.

16. The X-ray diagnosis apparatus of claim 13, wherein the processing circuitry is further configured to:

acquire an image processing parameter based on a pixel value in the region of interest, and perform image processing on the X-ray image using the image processing parameter.

17. The X-ray diagnosis apparatus of claim 13,
wherein the X-ray diaphragm is configured to restrict a region to be irradiated with the X-rays emitted from the X-ray generator, and
wherein the processing circuitry is further configured to:
control the X-ray diaphragm based on the region of interest.

* * * * *